US012640249B2

(12) United States Patent
Niri et al.

(10) Patent No.: US 12,640,249 B2
(45) Date of Patent: May 26, 2026

(54) METHOD AND SYSTEM FOR MEASURING AND ANALYZING BODY MOVEMENT, POSITIONING AND POSTURE

(71) Applicant: FLEX ARTIFICIAL INTELLIGENCE INC., Vancouver (CA)

(72) Inventors: Amin Niri, Vancouver (CA); Connor Gill, Vancouver (CA); Amol Gharat, Burnaby (CA)

(73) Assignee: Flex Artificial Intelligence Inc., Vancouver (CA)

( * ) Notice: Subject to any disclaimer, the term of this patent is extended or adjusted under 35 U.S.C. 154(b) by 956 days.

(21) Appl. No.: 17/618,269

(22) PCT Filed: Jun. 19, 2020

(86) PCT No.: PCT/CA2020/050865
§ 371 (c)(1),
(2) Date: Dec. 10, 2021

(87) PCT Pub. No.: WO2020/252599
PCT Pub. Date: Dec. 24, 2020

(65) Prior Publication Data
US 2022/0310226 A1 Sep. 29, 2022

Related U.S. Application Data

(60) Provisional application No. 62/865,052, filed on Jun. 21, 2019.

(51) Int. Cl.
*G09B 19/00* (2006.01)
*A61B 5/00* (2006.01)
(Continued)

(52) U.S. Cl.
CPC ........... *G16H 20/30* (2018.01); *A61B 5/1123* (2013.01); *A61B 5/1128* (2013.01); *A61B 5/741* (2013.01);
(Continued)

(58) Field of Classification Search
CPC . G09B 19/00; A63B 24/0062; A63B 24/0068; A63B 24/0071; A63B 24/0075; A63B 2220/806
See application file for complete search history.

(56) References Cited

U.S. PATENT DOCUMENTS

| | | | |
|---|---|---|---|
| 4,350,336 A | 9/1982 | Hanford | |
| 4,533,136 A | 8/1985 | Smith et al. | |

(Continued)

FOREIGN PATENT DOCUMENTS

| | | | |
|---|---|---|---|
| CA | 2048031 A1 | 1/1992 | |
| CA | 2253175 C | 5/1999 | |

(Continued)

OTHER PUBLICATIONS

US 5,704,877 A, 01/1998, Henry et al. (withdrawn)
(Continued)

*Primary Examiner* — Kurt Fernstrom
(74) *Attorney, Agent, or Firm* — McMillan LLP

(57) ABSTRACT

One aspect of the invention provides a computer-based method for providing corrective feedback about exercise form, the method comprising; recording a user performing a specific exercise: evaluating, by the computer, with machine learning, computer vision, or deep learning models that have been previously trained in order to evaluate the form of a user by training on labelled and or unlabeled datasets that consist of: both correct and incorrect exercise form for the different types of exercises being evaluated; identifying the user throughout the video, the exercise type, each repetition
(Continued)

of the exercise, the user's errors in form; and then generating, by the computer, corrective feedback for the user on how to improve exercise form for subsequent repetitions; and communicating, via an output device, the corrective feedback to the user.

21 Claims, 15 Drawing Sheets

(51) Int. Cl.

| | |
|---|---|
| *A61B 5/11* | (2006.01) |
| *G06T 7/73* | (2017.01) |
| *G06V 20/40* | (2022.01) |
| *G06V 40/20* | (2022.01) |
| *G16H 20/30* | (2018.01) |
| *G16H 40/63* | (2018.01) |
| *G16H 50/20* | (2018.01) |

(52) U.S. Cl.
CPC .............. *A61B 5/7435* (2013.01); *G06T 7/75* (2017.01); *G06V 20/46* (2022.01); *G06V 40/23* (2022.01); *G16H 40/63* (2018.01); *G16H 50/20* (2018.01); *A61B 2505/09* (2013.01); *G06T 2207/20132* (2013.01)

(56) References Cited

U.S. PATENT DOCUMENTS

| | | | |
|---|---|---|---|
| 4,591,147 A | 5/1986 | Smith et al. |
| 4,695,050 A | 9/1987 | Smith et al. |
| 4,790,530 A | 12/1988 | Maag |
| 4,822,038 A | 4/1989 | Maag |
| 4,838,543 A | 6/1989 | Armstrong et al. |
| 4,838,548 A | 6/1989 | Maag |
| 4,840,373 A | 6/1989 | Maag |
| 4,883,270 A | 11/1989 | Maag |
| 4,917,379 A | 4/1990 | Maag |
| 4,974,831 A | 12/1990 | Dunham |
| 5,007,630 A | 4/1991 | Real et al. |
| 5,085,426 A | 2/1992 | Wanzer et al. |
| 5,085,430 A | 2/1992 | Habing |
| 5,129,872 A | 7/1992 | Dalton et al. |
| 5,129,873 A | 7/1992 | Henderson et al. |
| 5,190,513 A | 3/1993 | Habing et al. |
| 5,199,935 A | 4/1993 | Gibson et al. |
| 5,253,915 A | 10/1993 | Schnader et al. |
| 5,308,304 A | 5/1994 | Habing |
| 5,318,490 A | 6/1994 | Henderson et al. |
| 5,320,588 A | 6/1994 | Wanzer et al. |
| 5,322,491 A | 6/1994 | Wanzer et al. |
| 5,366,432 A | 11/1994 | Habing et al. |
| 5,383,828 A | 1/1995 | Sands et al. |
| 5,417,634 A | 5/1995 | Habing |
| 5,435,798 A | 7/1995 | Habing et al. |
| 5,554,086 A | 9/1996 | Habing et al. |
| 5,580,337 A | 12/1996 | Habing et al. |
| 5,597,257 A | 1/1997 | Habing |
| 5,685,804 A | 11/1997 | Whan-Tong et al. |
| 5,709,632 A | 1/1998 | Socwell |
| 5,803,882 A | 9/1998 | Habing et al. |
| 5,885,193 A | 3/1999 | Habing et al. |
| 5,897,461 A | 4/1999 | Socwell |
| 5,897,467 A | 4/1999 | Habing et al. |
| 5,971,895 A | 10/1999 | Habing |
| 6,013,011 A | 1/2000 | Moore et al. |
| 6,080,091 A | 6/2000 | Habing et al. |
| 6,123,650 A | 9/2000 | Birrell |
| 6,146,313 A | 11/2000 | Whan-Tong et al. |
| 6,162,152 A | 12/2000 | Kuo |
| 6,165,107 A | 12/2000 | Birrell |
| 6,238,321 B1 | 5/2001 | Arnold et al. |
| 6,450,967 B1 | 9/2002 | Wu |
| 6,475,122 B2 | 11/2002 | Wu |
| 6,478,720 B1 | 11/2002 | Barker |
| 6,482,130 B1 | 11/2002 | Pasero et al. |
| 6,561,952 B2 | 5/2003 | Wu |
| 6,561,961 B2 | 5/2003 | Wu |
| 6,589,138 B2 | 7/2003 | Dyer et al. |
| 6,677,740 B1 | 1/2004 | Chen et al. |
| 6,710,491 B2 | 3/2004 | Wu et al. |
| 6,837,124 B2 | 1/2005 | Tsai et al. |
| 6,840,892 B1 | 1/2005 | Wu |
| 6,846,274 B2 | 1/2005 | Lopez-Santillana et al. |
| 6,906,503 B2 | 6/2005 | Lopez-Santillana et al. |
| 6,921,356 B1 | 7/2005 | Habing et al. |
| 6,939,271 B1 | 9/2005 | Whan-Tong et al. |
| 6,942,603 B1 | 9/2005 | Tsai et al. |
| 6,945,915 B2 | 9/2005 | Wu |
| 6,964,614 B1 | 11/2005 | Tsai |
| 7,014,597 B2 | 3/2006 | Tsai |
| 7,044,893 B2 | 5/2006 | Tsai |
| 7,071,589 B2 | 7/2006 | Bramel et al. |
| 7,090,623 B2 | 8/2006 | Stewart et al. |
| 7,094,180 B2 | 8/2006 | Huang et al. |
| 7,104,927 B2 | 9/2006 | Tsai |
| 7,156,777 B2 | 1/2007 | Dyer et al. |
| 7,374,522 B2 | 5/2008 | Arnold |
| 7,507,187 B2 | 3/2009 | Dyer et al. |
| 7,621,846 B2 | 11/2009 | Ainsworth et al. |
| 7,691,034 B2 | 4/2010 | May et al. |
| 7,704,192 B2 | 4/2010 | Dyer et al. |
| 7,708,672 B2 | 5/2010 | Gibson et al. |
| 7,731,634 B2 | 6/2010 | Stewart et al. |
| 7,731,635 B2 | 6/2010 | Dyer |
| 7,747,593 B2 | 6/2010 | Patterson et al. |
| 7,758,469 B2 | 7/2010 | Dyer et al. |
| 7,758,472 B2 | 7/2010 | Stewart |
| 7,780,577 B2 | 8/2010 | Arnold |
| 7,815,547 B2 | 10/2010 | Wu |
| 7,815,554 B2 | 10/2010 | Gibson et al. |
| 7,833,133 B2 | 11/2010 | Stewart et al. |
| 7,871,357 B2 | 1/2011 | Gibson et al. |
| 7,874,963 B2 | 1/2011 | Grind |
| 7,887,465 B2 | 2/2011 | Uffelman |
| 7,901,323 B2 | 3/2011 | Olason et al. |
| 7,922,625 B2 | 4/2011 | Grind |
| 7,951,098 B2 | 5/2011 | Wu et al. |
| 7,955,219 B2 | 6/2011 | Birrell et al. |
| 8,078,426 B2 | 12/2011 | Pipinich et al. |
| 8,105,250 B2 | 1/2012 | Wu |
| 8,157,706 B2 | 4/2012 | Ainsworth et al. |
| 8,221,292 B2 | 7/2012 | Barker et al. |
| 8,303,470 B2 | 11/2012 | Stewart et al. |
| 8,317,663 B2 | 11/2012 | Stewart et al. |
| 8,556,779 B2 | 10/2013 | Grind |
| 8,613,689 B2 | 12/2013 | Dyer et al. |
| 8,672,814 B2 | 3/2014 | Hopkins |
| 8,827,870 B2 | 9/2014 | Dyer et al. |
| 8,862,238 B2 | 10/2014 | Rahimi et al. |
| 8,944,961 B2 | 2/2015 | Ainsworth et al. |
| 9,161,708 B2 | 10/2015 | Elliott et al. |
| 9,174,085 B2 | 11/2015 | Foley et al. |
| 9,186,537 B2 | 11/2015 | Arnold et al. |
| 9,272,181 B2 | 3/2016 | Arnold et al. |
| 9,320,937 B2 | 4/2016 | Thompson |
| 9,358,426 B2 | 6/2016 | Aragones et al. |
| 9,367,668 B2 | 6/2016 | Flynt et al. |
| 9,418,571 B2 | 8/2016 | Younger |
| 9,430,920 B2 | 8/2016 | Munro et al. |
| 9,586,085 B2 | 3/2017 | Arnold et al. |
| 9,589,207 B2 | 3/2017 | Holohan |
| 9,597,540 B2 | 3/2017 | Arnold |
| 9,636,543 B2 | 5/2017 | Dyer et al. |
| 9,724,566 B2 | 8/2017 | Birrell |
| 9,761,011 B2 | 9/2017 | Utsunomiya et al. |
| 9,953,459 B2 | 4/2018 | Pavlidis et al. |
| 9,959,517 B2 | 5/2018 | Mourra |
| 9,973,814 B1 | 5/2018 | Henderson et al. |
| 9,986,415 B2 | 5/2018 | Cao |
| 9,996,065 B2 | 6/2018 | Yang et al. |
| 10,065,062 B2 | 9/2018 | Stewart |
| 10,176,171 B1 | 1/2019 | Patterson et al. |

(56) References Cited

U.S. PATENT DOCUMENTS

| | | | |
|---|---|---|---|
| 10,343,008 B2 | 7/2019 | Pullins et al. | |
| 10,395,119 B1* | 8/2019 | Vaden | G06V 20/41 |
| 10,466,963 B2 | 11/2019 | Levi et al. | |
| 10,486,016 B2 | 11/2019 | Robert et al. | |
| 10,668,314 B2 | 6/2020 | Mayer et al. | |
| 10,698,654 B2 | 6/2020 | Loughrey et al. | |
| 10,726,738 B1* | 7/2020 | Li | G09B 19/0038 |
| 10,792,495 B2 | 10/2020 | Izvorski et al. | |
| 10,864,406 B2 | 12/2020 | Foley et al. | |
| 10,898,760 B2 | 1/2021 | Packles et al. | |
| 10,949,658 B2 | 3/2021 | Brown et al. | |
| 11,056,105 B2 | 7/2021 | Robinson et al. | |
| 11,074,280 B2 | 7/2021 | Dobrynin et al. | |
| 11,141,624 B2 | 10/2021 | Wu | |
| 11,338,190 B2 | 5/2022 | Evancha et al. | |
| 11,340,925 B2 | 5/2022 | Mukherjee et al. | |
| 11,344,786 B2 | 5/2022 | Intonato et al. | |
| 2003/0166434 A1 | 9/2003 | Lopez-Santillana et al. | |
| 2005/0075850 A1 | 4/2005 | Wu et al. | |
| 2005/0238182 A1 | 10/2005 | Shih et al. | |
| 2006/0084422 A1 | 4/2006 | Huang et al. | |
| 2006/0089238 A1 | 4/2006 | Huang et al. | |
| 2006/0097038 A1 | 5/2006 | Huang et al. | |
| 2006/0116247 A1 | 6/2006 | Dyer et al. | |
| 2006/0135318 A1 | 6/2006 | Shih et al. | |
| 2006/0281604 A1 | 12/2006 | Stewart et al. | |
| 2007/0171664 A1 | 7/2007 | Shih et al. | |
| 2007/0179025 A1 | 8/2007 | Tsai | |
| 2007/0201727 A1 | 8/2007 | Birrell et al. | |
| 2007/0239088 A1 | 10/2007 | Wu | |
| 2008/0161163 A1 | 7/2008 | Stewart et al. | |
| 2013/0053218 A1 | 2/2013 | Barker | |
| 2013/0123667 A1* | 5/2013 | Komatireddy | A61B 5/746 |
| | | | 600/595 |
| 2013/0310221 A1 | 11/2013 | Zuber | |
| 2014/0172460 A1 | 6/2014 | Kohli | |
| 2014/0205980 A1* | 7/2014 | Braier | G09B 5/02 |
| | | | 434/247 |
| 2014/0257537 A1 | 9/2014 | Stroupe et al. | |
| 2015/0072797 A1* | 3/2015 | Sakyo | A63B 69/3632 |
| | | | 473/223 |
| 2015/0139502 A1 | 5/2015 | Holohan | |
| 2015/0324636 A1* | 11/2015 | Bentley | A63F 13/212 |
| | | | 386/227 |
| 2016/0256740 A1 | 9/2016 | Rowe | |
| 2016/0300347 A1* | 10/2016 | Dunn | G06T 7/0012 |
| 2017/0084007 A1 | 3/2017 | Rakhshanfar et al. | |
| 2017/0178309 A1 | 6/2017 | Rakhshanfar et al. | |
| 2017/0319906 A1 | 11/2017 | Chang et al. | |
| 2017/0368413 A1* | 12/2017 | Shavit | A63B 24/0075 |
| 2018/0050255 A1* | 2/2018 | Maani | G06V 40/23 |
| 2018/0336049 A1 | 11/2018 | Mukherjee et al. | |
| 2019/0091515 A1 | 3/2019 | Shavit et al. | |
| 2019/0217144 A1 | 7/2019 | Petrillo et al. | |
| 2019/0290964 A1 | 9/2019 | Oren | |
| 2019/0295436 A1 | 9/2019 | Rubinstein et al. | |
| 2021/0154517 A1 | 5/2021 | Petrillo et al. | |
| 2022/0108470 A1 | 4/2022 | Brown et al. | |
| 2022/0108476 A1 | 4/2022 | Zhang | |
| 2022/0148296 A1 | 5/2022 | Brown et al. | |
| 2024/0082638 A1* | 3/2024 | Shah | G06F 1/163 |

FOREIGN PATENT DOCUMENTS

| | | | |
|---|---|---|---|
| CA | 2236774 C | 1/2005 | |
| CA | 2687166 C | 7/2009 | |
| CA | 2689927 A1 | 10/2009 | |
| CN | 108734104 A | 11/2018 | |
| DE | 20100276 U1 | 4/2001 | |
| DE | 20206517 U1 | 9/2002 | |
| DE | 20213149 U1 | 1/2003 | |
| DE | 10153895 A1 | 5/2003 | |
| DE | 20308757 U1 | 9/2003 | |
| DE | 10247369 B3 | 4/2004 | |
| DE | 10248035 A1 | 5/2004 | |
| DE | 10258197 A1 | 7/2004 | |
| DE | 202005013897 U1 | 11/2005 | |
| DE | 102004020027 A1 | 12/2005 | |
| DE | 102005047996 A1 | 4/2006 | |
| DE | 202006003141 U1 | 5/2006 | |
| EP | 0956884 B1 | 8/2004 | |
| EP | 1943997 A1 | 7/2008 | |
| EP | 1844749 B1 | 4/2009 | |
| EP | 2177196 A1 | 4/2010 | |
| EP | 2042146 B1 | 12/2010 | |
| EP | 2067505 B1 | 5/2011 | |
| EP | 2383020 A1 | 11/2011 | |
| EP | 2626114 A1 | 8/2013 | |
| EP | 3000507 A1 | 3/2016 | |
| FR | 2869549 B1 | 7/2006 | |
| FR | 2870074 B1 | 7/2006 | |
| GB | 2270007 B | 5/1994 | |
| GB | 2294206 B | 10/1996 | |
| GB | 2385421 B | 2/2004 | |
| GB | 2413093 A | 10/2005 | |
| GB | 2413094 A | 10/2005 | |
| GB | 2412974 B | 6/2008 | |
| GB | 2539946 B | 2/2019 | |
| JP | H10225531 A | 8/1998 | |
| JP | 2008049171 A | 3/2008 | |
| WO | 2001011776 A1 | 2/2001 | |
| WO | 2011130561 A1 | 10/2011 | |
| WO | 2014145711 A1 | 9/2014 | |
| WO | 2020028883 A1 | 2/2020 | |
| WO | 2020129025 A1 | 6/2020 | |
| WO | 2020188425 A1 | 9/2020 | |

OTHER PUBLICATIONS

Parmar, P. et al., "Measuring the Quality of Exercises", 2016 38th Annual International Conference of the IEEE Engineering in Medicine and Biology Society (EMBC), IEEE, Aug. 16, 2016, pp. 2241-2244.

Díaz-Pereira, M. Pino. "Automatic recognition and scoring of Olympic rhythmic gymnastic movements", Human Movement Science, vol. 34, Feb. 4, 2014, pp. 63-80.

Kanojia, G. et al., "Attentive Spatio-Temporal Representation Learning for Diving Classification", 2019 IEEE/CVC Conference on Computer Vision and Pattern Recognition Workshops (CVPRW), IEEE, Jun. 16, 2019, pp. 2467-2476.

Zhdanov, P. et al., "Improving Human Action Recognition through Hierarchical Neural Network Classifiiers", 2018 International Joint Conference on Neural Networks (IJCNN), IEEE, Jul. 8, 2018, pp. 1-7.

Baptista, R. et al., "Video-Based Feedback for Assisting Physical Activity", VISIGRAPP 2017, pp. 274-280, Feb. 25, 2017.

Andriluka, M. et al., "2D Human Pose Estimation: New Benchmark and State of the Art Analysis", IEEE Computer Vision and Pattern Recognition, CVPR, 2014.

Gkioxari, G. et al., "Actions and Attributes from Wholes and Parts", arXiv: 1412.2604, May 2015.

Jaiswal. A. et al., "CapsuleGAN: Generative Adversarial Capsule Network", arXiv: 1802.06167, Feb. 2018.

Alonde, R. et al., "Capsules for Object Segmentation", arXiv: 1804.04241, Apr. 2018.

Wei, S. et al., "Convolutional Pose Machines", IEEE Computer Vision and Pattern Recognition, CVPR, 2016.

He, K. et al., "Deep Residual Learning for Image Recognition", arXiv: 1512.00385, Dec. 2015.

Toshev, A. et al., "DeepPose: Human Pose Estimation via Deep Neural Networks", arXiv: 1312.4659, Aug. 2014.

Guler, R. A. et al., "DensePose: Dense Human Pose Estimation In The Wild", arXiv: 1802.00434, Feb. 2018.

Chen, X. et al., "Detect What You Can: Detecting and Representing Objects Using Holistic Models And Body Parts", CBMM Memo No. 015, Jun. 2014.

Cai, Y. et al., "Weakly Supervised Human Body Detection Under Arbitrary Poses", IEEE International Conference on Image Processing, 2016.

(56)     References Cited

OTHER PUBLICATIONS

Sabour, S. et al., "Dynamic Routing Between Capsules", arXiv: 1710.09829, Nov. 2017.

Ren, S. et al., "Faster R-CNN: Towards Real-Time Object Detection with Region Proposal Networks", arXiv: 1506.01497, Jan. 2016.

Lin, T. et al., "Feature Pyramid Networks for Object Detection", arXiv: 1612.03144, Apr. 2017.

Simon, T. et al., "Hand Keypoint Detection in Single Images using Multiview Bootstrapping", IEEE Computer Vision and Pattern Recognition, CVPR, 2017.

Deng, J. et al., "ImageNet: A Large-Scale Hierarchical Image Database", IEEE Computer Vision and Pattern Recognition, CVPR, 2009.

He, K. et al., "Mask R-CNN", arXiv: 1703.06870, Jan. 2018.

Lin, Y. et al., "Microsoft COCO: Common Objects in Context", arXiv: 14050312, Feb. 2015.

Tran, D. et al., "Learning Spatiotemporal Features with 3D Convolutional Networks", arXiv: 1412.0767, Oct. 2015.

Bourdev, L. et al., "Poselets: Body Part Detectors Trained Using 3D Human Pose Annotations", ICCV, Sep. 2009.

Kay, W. et al., "The Kinetics Human Action Video Dataset", arXiv: 1705.06950, May 2017.

Shotton, J. et al., "Real-Time Human Pose Recognition in Parts from Single Depth Images", Microsoft Research Cambrige & Xbox Incubation, 2011.

Cao, Z. et al., "Realtime Multi-Person 2D Pose Estimation using Part Affinity Fields", arXiv: 1611.08050, Apr. 2017.

Girshick, R. et al., "Fast R-CNN", arXiv: 1504.08083, Sep. 2015.

Girshick, R. et al., "Region-based Convolutional Networks for Accurate Object Detection and Segmentation", IEEE Transactions on Pattern Analysis and Machine Intelligence, May 2015.

* cited by examiner

200

224 — Per Error Type 38'

Exercise Error Types 38 Corresponding to Exercise Type 28

226 — Per Rep Video 36A' in Set 36A

Labelled Rep Video Set 36A

228 — Error?

No?

Yes?

230 — Add Error Type and Error Period to Video 36A'

232 — Add Error Type and Correct Label to Video 36A'

Training Video Set 36B

400

410 — Detect Exercise Object 62

412 — Calculate Object Height 68

416 — Calculate Running Average 72 of Object Height

418 — Determine Crossing Frames 74

420 — Pair Up/Down Crossing Frames into Pairs 74'

422 — Determine Minima 76 (76A, 76B) of Object Height 68 Between Crossing Frame Pairs 74'

424 — Parse Video by Mimima 76A, 76B

Exercise Object 66 of Exercise Type 64

Video 60 of Rep 62

Rep Videos 78

METHOD AND SYSTEM FOR MEASURING AND ANALYZING BODY MOVEMENT, POSITIONING AND POSTURE

REFERENCE TO RELATED APPLICATIONS

This application claims priority from application No. 62/865,052, filed 21 Jun. 2019. For purposes of the United States, this application claims the benefit under 35 U.S.C. § 119 of application No. 62/865,052, filed 21 Jun. 2019, and entitled METHOD AND SYSTEM FOR MEASURING AND ANALYZING BODY MOVEMENT, POSITIONING AND POSTURE which is hereby incorporated herein by reference for all purposes.

TECHNICAL FIELD

The technology described herein generally relates to use of recorded video data for evaluating correctness of, and/or identifying potential problems with, an individual's exercise form, athletic movement, posture, or other human action. The technology more particularly relates to evaluating an individual's exercise form, athletic movement, posture, or other human action by machine learning, computer vision, and deep learning models trained on datasets comprising previously recorded exercises, various human activities and actions, human poses in a variety of postures and movements, and providing feedback on the individual's exercise form, athletic movement, posture, or other human action.

BACKGROUND

Computer vision technology has improved significantly in the last half decade to the point that it is now possible for a computer to locate and identify various aspects and/or parts of the human body and actions, locate and track objects in real-time video streams (object detection and localization), classify objects in images and videos, as well as a wide variety of useful real-world tasks.

Progress in the field has been accelerated due to novel accessibility to large datasets like DeepMind's Kinetics™, Microsoft COCO™, and Facebook's DensePose-COCO™. The acceleration gained by these datasets has been coupled with the advancement of machine learning, computer vision, and deep learning algorithms. These new, more powerful algorithms include, but are not limited to: ResNet, Faster R-CNN, C3D, and CapsNet. Furthermore, human pose estimation algorithms include: OpenPose, DeepPose, and DensePose. These advancements have allowed progress in areas such as object detection, object localization, and video recognition to name a few.

Prior art has attempted to extend these advancements into real-world applications. For example, Face++ produces a body detection API which outputs bounding boxes around humans in images (i.e. object localization) and a body outlining API that produces the pixels corresponding to each human in an image (i.e. instance segmentation). See, e.g., https://www.faceplusplus.com. Also, SenseTime uses body part feature points in its core technologies, which incorporate positioning body feature points on mobile terminals to provide real-time localization for body part localization and angular movement identification.

There is a general desire for methods and systems for evaluating an individual's exercise form, athletic movement, posture, and/or other human action involving automated detection of potential problems with the individual's exercise form, athletic movement, posture and/or other human action from a video of the individual performing the exercise, athletic movement, posture and/or other human action.

The foregoing examples of the related art and limitations related thereto are intended to be illustrative and not exclusive. Other limitations of the related art will become apparent to those of skill in the art upon a reading of the specification and a study of the drawings.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

One aspect of the invention provides a computer-based method for providing corrective feedback about exercise form of a possibly previously unseen user, the method performed on at least one computer having a processor, a memory and input/output capability. The method comprises: recording, via any video recording technology, while a user performs a specific exercise; preprocessing, by a computer which can potentially be the video recording device, the video into the correct input format for the machine learning methods utilized; evaluating, by the computer, with machine learning, computer vision, and/or deep learning models that have been previously trained in order to evaluate the form of a user by training on labelled and or unlabeled datasets that comprise or consist of: a variety of human poses performing various actions and postures, various activities performed by humans, different types of exercises, and both correct and incorrect exercise form for the different types of exercises being evaluated from as wide a variety of demographic as possible; identifying the user throughout the video, the exercise type, each repetition of the exercise, the user's errors in form; and then generating, by the computer, corrective feedback for the user on how to improve exercise form for subsequent repetitions; and communicating, via an output device, the corrective feedback to the user.

In some embodiments, the corrective feedback is created to improve the quality and safety of a user's exercise form.

In some embodiments, the corrective feedback consists of verbal, written, and/or visual feedback on body part position, movement, potential causations of their form failures, and suggested steps to correct said form failure.

In some embodiments, newly collected data may be added periodically to the datasets, which are then regularly used to retrain the models in order to potentially improve their predictive power.

In some embodiments, the recording of the exercise of the user takes place at one location; a computer which is situated locally or remotely, potentially the same device as the video recording device; and if the video recording device and computer are not the same device, the video data is transmitted to the computer.

In some embodiments, the output device is in the same location as the video recording device.

In some embodiments, the datasets consist of: human poses in varying actions and postures, various actions performed by humans, different exercise types, and both correct and incorrect exercise form.

In some embodiments, the exercises are selected from: squat, deadlift, bench press, or other movements, including any variation of these movements.

Some embodiments comprise evaluating the video recording of the user by computer vision, machine learning, and deep learning techniques that have learned to identify a prototypical human pose consisting of a variety of body part locations, human performed actions, exercise type and form; all derived by the models from previously seen visual data.

One aspect of the invention provides an apparatus for evaluating a user's exercise form and providing feedback to the user, the apparatus comprising: a single video recording device (which may or may be not worn by the subject), and which records video of the user performing an exercise movement; possibly a transmission channel if necessary for communicating data to one or more computing devices wherein the one or more computing devices each comprises a memory, output device, and one or more processors configured with instructions to: preprocess videos into proper input format for models; evaluate the video of the user by computer vision, machine learning, and deep learning algorithms trained on datasets (with or without labels/annotations) comprising or consisting of previously recorded human poses, exercise types and form; generate user-appropriate feedback to correct the user's exercise form; and communicating, via the output device, the feedback to the user, generated by the computer. The transmission may not be necessary if the described instructions above are configured on the recording device itself.

In some embodiments, the feedback is designed to educate the user about failures in proper form and correct the user's exercise form.

The technology herein includes a computer-based method for evaluating exercise form of a user, the method being performed on at least one computer, the computer having a processor, a memory, and input/output capability. The method comprises: video recording of an exercise motion performed by the user, wherein the exercise motion is encapsulated in the raw video data; which is parsed and formatted, by a computer, into the proper format for the algorithms used; evaluating, by the computer, the user's exercise from the video through machine learning, computer vision, and deep learning algorithms developed with the datasets that the models were trained on, wherein each dataset comprises: human poses in varying actions and postures, human actions and activities, various exercise types, and both correct and incorrect exercise form; identifying: a user's location in each video frame, type of exercise being performed, each repetition of the identified exercise; and communicating, via an output device, corrective suggestions for the user, which improve exercise form on future occasions.

One aspect of the invention provides a method of generating user feedback from video of a user performing one or more reps of an exercise type, the method comprising: receiving an exercise type; selecting a rep detection model from a plurality of rep detection models, wherein the selected rep detection model corresponds to the exercise type; selecting an error indication model from a plurality of error indication models, wherein the selected error indication model corresponds to the exercise type; receiving a video of a user performing one or more reps of the exercise type; identifying a rep in the video with the selected rep detection model; generating a form error indication for the rep with the selected error indication model; and generating feedback based on the form error indication.

In some embodiments, receiving the exercise type comprises receiving a user selection of one of a plurality of exercise types.

In some embodiments, receiving the exercise type comprises generating an exercise type for the video with an exercise classification model.

In some embodiments, receiving the video of the user performing one or more reps of the exercise type comprises capturing video of the user performing the reps with a video capture device.

In some embodiments, the video comprises a plurality of frames, and identifying a rep in the video with the selected rep detection model comprises: identifying an object region in each frame of the video containing an exercise object, wherein the exercise object corresponds to the exercise type; calculating an object height for each frame based on the object region in each frame; calculating a running average of the object height for each frame; determining a plurality of up-crossing frames, wherein each up-crossing frame is a frame with an object height equal to the running average for the frame and each up-crossing frame follows a frame with an object height less than the running average for the frame; determining a plurality of down-crossing frames wherein each down-crossing frame is a frame with an object height equal to the running average for the frame and each down-crossing frame follows a frame with an object height greater than the running average for the frame; generating a plurality of crossing point pairs by associating each up-crossing frame with one of the down-crossing frames; determining a plurality of minima frames wherein each minima frame is a frame between two of the crossing point pairs and the object height for each minima frame is the minimum object height for all frames between the two crossing point pairs; identifying a rep start frame, wherein the rep start frame is one of the minima frames preceding one of the crossing point pairs; identifying a rep end frame, wherein the rep end frame is one of the minima frames following the one of the crossing point pairs; and identifying the rep as comprising the frames between the rep start frame and the rep end frame.

In some embodiments, detecting the rep in the video with the selected rep detection model comprises: smoothing the object height for each frame between the rep start frame and rep end frame; calculating a slope of the object height for each frame between the rep start frame and rep end frame; determining one or more slope-crossing frames between the rep start frame and rep end frame where the slope for the frame equals a threshold slope; updating the rep start frame to the first slope-crossing frame if the slope at the first slope-crossing frame is positive; and updating the rep end frame to the last slope-crossing frame if the slope at the last slope-crossing frame is negative.

In some embodiments, smoothing the object height for each frame between the rep start frame and rep end frame comprises averaging the object height of each frame with the object height of a first number of frames preceding each frame and the object height of a second number of frames following each frame.

In some embodiments, calculating the slope of the object height for each frame comprises dividing a sum of the object height of the preceding frame and the object height of the following frame with a sum of a maximum object height of all frames between the rep start frame and the rep end frame and a minimum object height of all frames between the rep start frame and the rep end frame.

Some embodiments comprise cropping the video to a specific aspect ratio.

Some embodiments comprise adding pixels to the video to format the video to a specific aspect ratio.

In some embodiments, the specific aspect ratio is one pixel by one pixel.

In some embodiments, the video comprises a plurality of frames, and generating the form error indication for the detected rep with the selected error indication model comprises: generating an error indication for each frame of the rep; and generating the form error indication based at least in part on the error indication for at least one frame of the rep.

In some embodiments, the error indication for each frame of the rep comprises an error probability, and generating the form error indication based at least in part on the error indication for at least one frame of the rep comprises generating a form error indication indicating the presence of an error if the error probability for at least one frame of the rep exceeds a probability threshold.

In some embodiments, the error indication for each frame of the rep comprises an error probability, and generating the form error indication based at least in part on the error indication for at least one frame of the rep comprises generating a form error indication indicating the presence of an error if the error probability for a threshold number of frames of the rep exceed a probability threshold.

In some embodiments, the error indication for each frame of the rep comprises an error probability, and generating the form error indication based at least in part on the error indication for at least one frame of the rep comprises generating a form error indication indicating the presence of an error if the error probability for a threshold number of consecutive frames of the rep exceed a probability threshold.

In some embodiments, the error indication for each frame of the rep comprises an error probability, and generating the form error indication based at least in part on the error indication for at least one frame of the rep comprises: calculating a sum of the error probabilities of the frames of the rep; and generating a form error indication indicating the presence of an error if the sum of the error probabilities exceeds a probability threshold.

In some embodiments, generating feedback based on the form error indication comprises selecting a media file corresponding to an error type of the error indication model if the form error indication indicates the presence of an error in the rep.

In some embodiments, the media file comprises video of an individual demonstrating an error of the error type.

In some embodiments, the media file comprises corrective audio instructions.

In some embodiments, the media file comprises corrective video instructions.

In some embodiments, the method is performed by a processor of a computer system.

Some embodiments comprise a non-transitory medium having stored thereon computer-readable instructions, which when executed by a data processor, cause the data processor to execute any method herein disclosed.

One aspect of the invention provides a system for providing feedback to a user performing one or more reps of an exercise type, the system comprising: a video capture device; a processor; a memory module; an input module; and an output module; wherein the processor is configured to: receive an exercise type; capture video of the user performing one or more reps of the exercise type with the video capture device; retrieve a rep detection model corresponding to the exercise type from the memory module; execute the rep detection model to identify a rep in the video; retrieve an error indication model corresponding to the exercise type from the memory module; execute the error indication model to generate a form error indication for the identified rep; and output feedback with the output module based on the form error indication.

In some embodiments, the processor is configured to receive the exercise type from the input module.

In some embodiments, the processor is configured to: retrieve an exercise classification model from the memory module; and execute the exercise classification model to generate the exercise type from the video.

In some embodiments, the video comprises a plurality of frames, and the processor is configured to: retrieve an object detection model from the memory module; execute the object detection model to detect an object region in each frame of the video; calculate an object height for each frame based on the object region in each frame; calculate a running average of the object height for each frame; determine a plurality of up-crossing frames, wherein each up-crossing frame is a frame with an object height equal to the running average for the frame and each up-crossing frame follows a frame with an object height less than the running average for the frame; determine a plurality of down-crossing frames wherein each down-crossing frame is a frame with an object height equal to the running average for the frame and each down-crossing frame follows a frame with an object height greater than the running average for the frame; generate a plurality of crossing point pairs by associating each up-crossing frame with a down-crossing frame; determine a plurality of minima frames wherein each minima frame is a frame between two of the crossing point pairs and the object height for each minima frame is the minimum object height for all frames between the two crossing point pairs; identify a rep start frame, wherein the rep start frame is one of the minima frames preceding one of the crossing point pairs; identify a rep end frame, wherein the rep end frame is one of the minima frames following the one of the crossing point pairs; and identify the rep as comprising the frames between the rep start frame and the rep end frame.

In some embodiments, the processor is configured to: smooth the object height for each frame between the rep start frame and rep end frame; calculate a slope of the object height for each frame between the rep start frame and rep end frame; determine one or more slope-crossing frames between the rep start frame and rep end frame where the slope for the frame equals a threshold slope; update the rep start frame to the first slope-crossing frame if the slope at the first slope-crossing frame is positive; and update the rep end frame to the last slope-crossing frame if the slope at the last slope-crossing frame is negative.

In some embodiments, the processor is configured to smooth the object height for each frame between the rep start frame and rep end frame by averaging the object height of each frame with the object height of a first number of frames preceding each frame and the object height of a second number of frames following each frame.

In some embodiments, the processor is configured to calculate the slope of the object height for each frame between the rep start frame and rep end frame by dividing a sum of the object height of the preceding frame and the object height of the following frame with a sum of a maximum object height of all frames between the rep start frame and the rep end frame and a minimum object height of all frames between the rep start frame and the rep end frame.

In some embodiments, the processor is configured to crop each frame of the video to a specific aspect ratio.

In some embodiments, the processor is configured to add pixels to each frame of the video to format the video to a specific aspect ratio.

In some embodiments, the specific aspect ratio is one pixel by one pixel.

In some embodiments, the video comprises a plurality of frames, and the processor is configured to: execute the error indication model to generate a form error indication for each frame of the rep; generate the form error indication based at least in part on the error indication for at least one frame of the rep.

In some embodiments, the error indication for each frame of the rep comprises an error probability, and the processor is configured to generate a form error indication indicating the presence of an error if the error probability for at least one frame of the rep exceeds a probability threshold.

In some embodiments, the error indication for each frame of the rep comprises an error probability, and the processor is configured to generate a form error indication indicating the presence of an error if the error probability for a threshold number of frames of the rep exceed a probability threshold.

In some embodiments, the error indication for each frame of the rep comprises an error probability, and the processor is configured to generate a form error indication indicating the presence of an error if the error probability for a threshold number of consecutive frames of the rep exceed a probability threshold.

In some embodiments, the error indication for each frame of the rep comprises an error probability, and the processor is configured to: calculate a sum of the error probabilities of the frames of the rep; and generate a form error indication indicating the presence of an error if the sum of the error probabilities exceeds a probability threshold.

In some embodiments, the processor is configured to retrieve the feedback comprising a media file from the memory module based at least in part on an error type of the form error indication model and the form error indication.

In some embodiments, the media file comprises video of an individual demonstrating an error of the error type, and the processor is configured to display the media file with the output module.

In some embodiments, the media file comprises audio instructions, and the processor is configured to play the media file with the output module.

In some embodiments, the media file comprises video of corrective instructions, and the processor is configured to display the media file with the output module.

In some embodiments, the video capture device comprises a video capture device of a mobile phone, a tablet computer, or a personal computer.

In some embodiments, the processor comprises a processor of a mobile phone, a tablet computer, or a personal computer.

In some embodiments, the memory module comprises one or more of: a hard disk drive, an optical data storage media, an electronic data storage media, a flash RAM, an EPROM, and a preprogrammed chip.

In some embodiments, the input module comprises one or more of a keyboard and a touch display.

In some embodiments, the output module comprises one or more of a speaker and a display.

One aspect of the invention provides a method of generating a rep start frame and a rep end frame for an exercise rep in a video of a user performing one or more exercise reps of an exercise type, the method comprising: receiving the video of the user performing the one or more exercise reps of the exercise type, wherein the video comprises a plurality of numbered frames; identifying an object region in each frame of the video containing an exercise object; calculating an object height for each frame based on the object region in each frame; calculating a running average of the object height for each frame; determining a plurality of up-crossing frames, wherein each up-crossing frame is a frame with an object height equal to the running average for the frame and each up-crossing frame follows a frame with an object height less than the running average for the frame; determining a plurality of down-crossing frames wherein each down-crossing frame is a frame with an object height equal to the running average for the frame and each down-crossing frame follows a frame with an object height greater than the running average for the frame; generating a plurality of crossing point pairs by associating each up-crossing frame with a down-crossing frame; determining a plurality of minima frames wherein each minima frame is a frame between two of the crossing point pairs and the object height for each minima frame is the minimum object height for all frames between the two crossing point pairs; generating a rep start frame, wherein the rep start frame is one of the minima frames preceding one of the crossing point pairs; and generating a rep end frame, wherein the rep end frame is one of the minima frames following the one of the crossing point pairs.

Some embodiments comprise smoothing the object height for each frame between the rep start frame and rep end frame; calculating a slope of the object height for each frame; determining one or more slope-crossing frames where the slope for the frame equals a threshold slope; changing the rep start frame to the first slope-crossing frame if the slope at the first slope-crossing frame is positive; and changing the rep end frame to the last slope-crossing frame if the slope at the last slope-crossing frame is negative.

Some embodiments comprise smoothing the object height for each frame between the rep start frame and rep end frame comprises averaging the object height of each frame with the object height of a first number of frames preceding each frame and the object height of a second number of frames following each frame.

Some embodiments comprise calculating the slope of the object height for each frame comprises dividing a sum of the object height of the preceding frame and the object height of the following frame with a sum of a maximum object height of all frames between the rep start frame and the rep end frame and a minimum object height of all frames between the rep start frame and the rep end frame.

Some embodiments comprise cropping the video between the rep start frame and the rep end frame.

In some embodiments, identifying the object region in each frame of the video containing the exercise object comprises identifying a bounding box in each frame of the video containing the exercise object.

In some embodiments, calculating the object height for each frame based on the object region in each frame comprises calculating a center of the object region.

In some embodiments, calculating the object height for each frame based on the object region in each frame comprises calculating a distance between a bottom of each frame and the center of the object region.

In some embodiments, the running average for each frame is the average of the object height for the 200 frames preceding each frame.

One aspect of the invention provides a method of generating training data for an error detection model from video of a user performing one or more exercise reps of an exercise type, the method comprising: receiving a video of a user performing one or more exercise reps of an exercise type; identifying a rep start frame and a rep end frame in the video;

identifying a rep video comprising the video frames between the rep start frame and the rep end frame; generating an exercise label of the rep video with an exercise classification model; confirming the exercise label matches the exercise type; identifying an error of an error type in the rep video; identifying an error start frame and an error end frame of the rep video; labelling the rep video with the error type, error start frame, and error end frame; identifying a relevant region in each frame of the rep video containing one or more error objects corresponding to the error type; and cropping the rep video based on the relevant region in each frame of the rep video.

In some embodiments, the exercise classification model comprises a machine learning algorithm.

One aspect of the invention provides a method of training an error indication model, the method comprising: generating training data according any method herein disclosed; and training an error indication model with the training data.

In some embodiments, the error indication model comprises a machine learning algorithm.

One aspect of the invention provides a method of generating a form error indication, the method comprising: capturing a video of a user performing one or more exercise reps of an exercise type; identifying a rep in the video according to any method herein disclosed; and generating a form error indication of the rep with an error indication model.

In some embodiments, the error indication model is trained according to any method herein disclosed.

One aspect of the invention provides a method of generating corrective feedback for a user performing an exercise movement, the method comprising: generating a form error indication according any method herein disclosed; and generating audio feedback based on the form error indication.

In some embodiments, the form error indication comprises an error type.

In some embodiments, receiving the video of the user performing one or more exercise reps of an exercise type comprises: searching an online database of videos for a video associated in the online database with the exercise type; and downloading the video associated with the exercise type from the online database.

In some embodiments, labelling the rep video with the error type, error start frame, and error end frame comprising storing the error type, error start frame, and error end frame in a relational database.

In some embodiments, labelling the rep video with the error type, error start frame, and error end frame comprising storing the error type, error start frame, and error end frame in a metadata associated with the rep video.

In some embodiments, the exercise type is one of: squats, deadlifts, pull-ups, push-ups, bench presses, planks, bicep curls, and a yoga pose.

In some embodiments, the exercise object is one of: a barbell, a dumbbell, a weight plate, a TRX™ band, a medicine ball, an elastic band, a skipping rope, and an exercise machine.

In addition to the exemplary aspects and embodiments described above, further aspects and embodiments will become apparent by reference to the drawings and by study of the following detailed descriptions.

BRIEF DESCRIPTION OF THE DRAWINGS

Exemplary embodiments are illustrated in referenced figures of the drawings. It is intended that the embodiments and figures disclosed herein are to be considered illustrative rather than restrictive.

DESCRIPTION

Figure 1A:
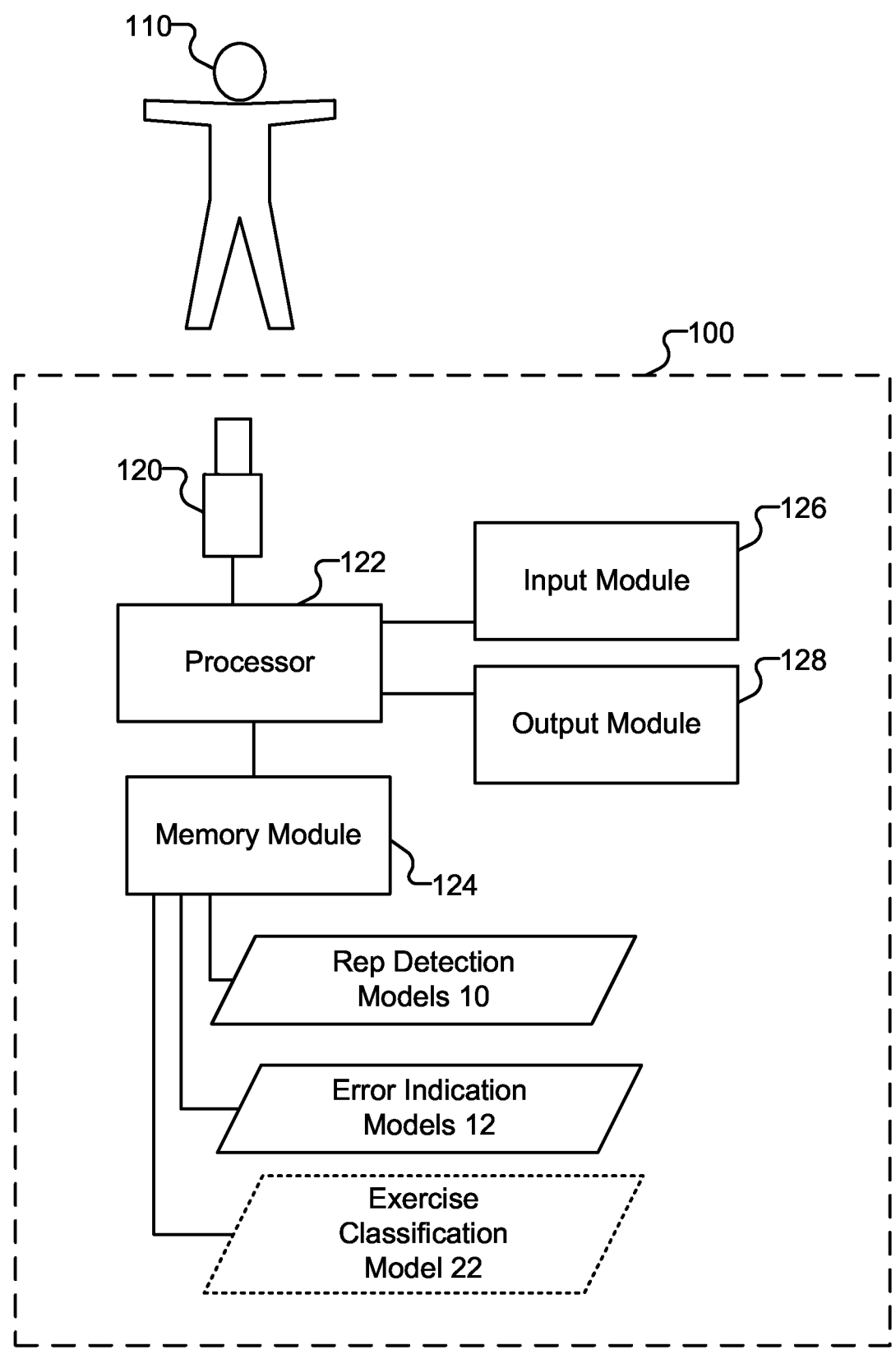
FIG. 1A depicts an exemplary system for detecting potential problems (e.g. form errors) of a user performing a physical exercise, according to one embodiment of the present invention.

Throughout the following description specific details are set forth in order to provide a more thorough understanding to persons skilled in the art. However, well known elements may not have been shown or described in detail to avoid unnecessarily obscuring the disclosure. Accordingly, the description and drawings are to be regarded in an illustrative, rather than a restrictive, sense.

Aspects of the technology described herein receive video of a user performing one or more repetitions (reps) of an exercise type, and provide feedback to the user on the user's form (e.g. potential problems with the user's form) when performing the reps shown in the video. Example exercise types include, but are not limited to: squats, deadlifts, pull-ups, push-ups, bench presses, planks, bicep curls, yoga poses, and/or the like. Exercises may include exercise objects, such as, by way of non-limiting example, a barbell, one or more dumbbells, weight plates, TRX™ bands, medicine balls, elastic bands, skipping ropes, exercise machines and/or the like. Such exercise objects are not necessary, however.

The technology may be configured to receive video of a user performing the exercise reps in any setting where the user may perform the reps. Example settings include, but are not limited to: a home, a gym, outdoors, a hotel room, a field, and the like.

The technology described herein may utilize any form of video capture apparatus, or a combination of two or more different types of video capture apparatus. The video capture apparatus may store captured video locally or remotely. The video capture apparatus may be configured to capture video of the user performing exercise reps in one or more of the settings. In a typical (but not limiting) scenario, a user might capture video of themselves performing an exercise using their mobile phone.

The technology described herein may utilize video capture apparatus and machine learning models to generate one or more form error indications from video of a user performing one or more reps of an exercise type (i.e. back squat, bicep curl, etc.), store the video and error indications, and use the error indications to provide feedback to the user on the user's form when performing the one or more reps shown in the video. The feedback may include corrective cues which may improve the user's exercise form.

Corrective cues may include audio and/or visual messages. For example:

an audio queue indicating the presence of one or more form errors;

an audio queue indication the presence of a specific form error;

an audio message describing a form error;

an audio message describing proper exercise form;

a video of an individual demonstrating a form error; and/or a video of an individual demonstrating proper exercise form.

Initially, a user records a video of themselves or another user performing one or more reps of an exercise type. The video may be transferred to a suitably programmed computer that formats the video into a format suitable for input to a machine learning model and/or computer vision algorithm. A suitably programmed computer could include a smartphone or other video capture device with similar computing capabilities with which the video was originally captured, thus not requiring transfer of the video to another computer.

For every exercise type, a set of predefined exercise errors (error types) may be identified and a separate error indication model may be trained for each of the exercise errors (error types) for each exercise type. The exercise errors (error types) may be related to one body part or a combination of two or more body parts. Each error indication model may generate an error indication for a respective error type of the exercise type. The error indication may comprise an error identification corresponding to the error type that the specific error indication model is trained for, a start frame of the error, and an end frame of the error.

To generate an error indication from user video, the video may be processed using an object detection model that detects suitable object(s) in each frame (or in each of a suitable subset of the frames) relevant to one or more exercise types for which the system is configured to detect error.

In some embodiments, the object detection model draws (or otherwise identifies) rectangular bounding boxes around the relevant object(s) in each frame of interest. The relevant objects may include one or more of: the body of the user performing the reps, one or more body parts (e.g. feet, knees, hips, hands, back, etc.) of the user performing the reps, and any equipment or exercise objects (e.g. barbells, dumbbells, etc.) used by the user to perform the exercise.

Once the relevant objects are detected in each frame of interest, a start frame and an end frame of one or more individual reps in the video may be identified. Individual reps may be identified by tracking one or more spatial coordinates of relevant objects between frames. For example, when performing reps with a barbell, the barbell's vertical position in each frame can be used to identify when a rep starts and ends. One or more of the individual reps may then be processed separately to generate one or more error indications for each individual rep.

Entire video frames of a user performing exercise reps may not be required to generate a form error indication for a given error, or to generate training data for training an error indication model for a given error. For example, to detect errors related to feet stability, feet positioning, balance on the feet and/or the like, it may be desirable to process only a portion of the video frames containing the individual's feet. Therefore, the video may be spatially cropped to include only, or otherwise focus on, the relevant objects for a given error. Such spatial cropping can reduce processing requirements and may increase the accuracy of the machine learning models. A video may be spatially cropped to generate a form error indication for the video, and also to prepare training data for training a given error indication model.

For example, to generate training data for an error indication model for a given error related to the position of a user's feet, a video may be spatially cropped to include only, or otherwise focus on, the user's feet. Similarly, to generate an error indication for video of a user performing reps, the video may be spatially cropped to include only, or otherwise focus on, the user's feet. The videos may be spatially cropped based on one or more bounding boxes generated by a relevant object detection model.

To identify a specific error (e.g. a particular error type for a particular exercise type), a specific recurrent neural network model with a 3D convolutional backbone may be trained using suitable training data. Each error indication model may be trained with training data comprising a set of rep videos labeled by expert annotators. Each rep video may be separately annotated for each error type, and the start frame and the end frame of any error along with an error type of the error may be identified in each rep video.

The input for each error indication model may comprise a series of video frames which together show a single rep and which contain the relevant objects for the error. The output of each error indication model may comprise a probability of the presence of the error for each frame of the video.

The presence or absence of a form error may be inferred from the output of an error indication model. Where the output of an error indication model is a probability of a form error per frame of a video, the presence of the form error in the video may be inferred when:

any frame in the video has an error probability exceeding a threshold probability;

a number of frames exceeding a frame threshold have an error probability exceeding a probability threshold;

a consecutive number of frames exceeding a frame threshold have an error probability exceeding a probability threshold; and/or a sum of all error probabilities for the frames of the video exceed an error sum threshold.

Once the user video is processed by all error detection models for a given exercise, the error indications of the models may be used to provide audio or visual feedback to the user.

The video capture apparatus utilized herein captures video of the user and their environment. The video, once properly formatted, allows for evaluation by a suitably trained object detection model to identify a user's location throughout the video. Suitably trained exercise identification models may also be utilized to determine or verify the exercise type shown in the video. Suitably trained error indication models may be utilized to determine one or more form errors for particular error types and for particular exercise types. The user video may be used to generate training data for one or more of the object detection model, exercise identification models, and/or error indication models.

The length of an exercise video is determined by many factors including the exercise type, the number of reps performed, and variations between specific users such as technical skill and fitness ability. Therefore, the length of an uncropped video may range from a few seconds to several minutes. In addition, video capture apparatus generally capture video at a rate of 30 frames per second (fps). The error detection models described herein may be configured to generate an error indication for videos of varying or different lengths, and varying or different frame rates.

The one or more computer systems used to perform some or all of the steps of the methods described herein may either be proximate a user and video capture device, or remote from the user and video capture device. Where one or more computer systems are remote from the user and video capture device, the video capture device and one or more of the remote computers may be connected through a network connection (e.g. WiFi, a LAN connection, a WAN connection and/or the like) to transmit captured video from the video capture device to the one or more remote computers. The one or more of the remote computers may be programmed to format the video into a format desired for input to the error indication models. The one or more of the remote computers may be programmed to generate one or more error indications of the formatted video, and provide feedback to the user based on the one or more error indications.

A user video may be evaluated, by machine learning and computer vision algorithms, that have been trained with a set of example videos of a variety of individuals performing the exercise. The set of example videos may comprise videos labelled with form errors, and without form errors (i.e. demonstrating proper form/technique). The set of example videos may also comprise videos of a variety of individuals performing exercises both with and without form errors. This variety of individuals may include, but is not limited to a variety of ages, genders, body weights and compositions, heights, skill levels, athletic abilities, etc.

User videos may be added to the set of example videos as users use the system, and the error indication models may be retrained (or the training of the error indication models may be updated) using user videos.

The example movement that will be referenced (without limitation) throughout this description to describe the array of measurable parameters and the operation of the methods and systems of various aspect of the invention is a back squat. The back squat exercise movement has the user standing with feet shoulder-distance apart and their feet pointing slightly outward, and with a barbell resting parallel to the ground on the user's upper back. As the user performs the exercise, the user's knees and hips bend as the user lowers their rear in a controlled manner as if sitting in a chair. The user stops descent once the tops of the user's thighs are parallel to the ground or lower. The user then reverses the motion and exerts enough upward force to return to a standing position.

Throughout the evaluation of an exercise movement, the data extracted from the video input may provide information about a location of a user, a location of body parts of the user, one or more angles of joints of the user, etc. This information can be derived from the user video using suitable object detection models to identify the user, the location of relevant body parts of the user, and exercise equipment such as a barbell. The vertical position of the barbell may be determined for the identification of the barbell in each frame, and the barbell's vertical position may be used to separate (either by parsing the video or indicating start frames and end frames) individual exercise reps in the video into rep videos. For each error to be detected, each rep video may be spatially cropped, such that each cropped rep video contains the relevant region (body parts and/or exercise objects) required to identify each respective error. The cropped rep videos may then be formatted to match a format of training videos used to train the error detection models. The error detection models identify the presence of error types of an exercise type. Various form errors may cause specific issues for an individual exhibiting the form error. For example, if a user's chest is identified as being insufficiently upright (a form error), the user may be placing unnecessary stress on their lumbar spine. Such a form error (insufficiently upright chest) may be one of the error types identified by an error detection model corresponding to the back squat exercise.

Once any issues with a user's exercise form have been identified, then feedback can be provided back to the user regarding whether the user's form is correct or not. Furthermore, the feedback may convey to the user what they can focus on while completing the exercise movement in the future in order to avoid exhibiting the form error.

FIG. 1A depicts system 100 for detecting potential problems (e.g. form errors) of user 110 performing one or more exercise reps of an exercise type, according to one exemplary embodiment of the present invention.

System 100 comprises video capture device 120, processor 122, memory module 124, input module 126, and output module 128. Video capture device 120, processor 122, memory module 124, input module 126, and output module 128 are communicatively coupled. All of video capture device 120, processor 122, memory module 124, input module 126, and output module 128 may be provided by a single device, for example a smartphone, tablet computer and/or the like. In some embodiments, parts of video capture device 120, processor 122, memory module, 124, input module 126 and/or output module 128 may be distributed (e.g. over a communication network or otherwise). For example, a first portion of memory module 124 may be local to the smartphone of user 110 and a second portion of memory module 124 may be resident on a server computer at some other location.

Video capture device 120 may be arranged to view user 110 and capture video 16 of user 110 performing an exercise rep 18 of exercise type 14. Exercise types 14 and reps 18 are described in more detail below.

Memory module 124 stores one or more rep detection models 10, and one or more error indication models 12. Each of rep detection models 10 corresponds to an exercise type. Each of error indication models 12 corresponds to a particular error type 38' within a corresponding exercise type. Error types 38' are described in more detail below.

Processor 122 of system 100 may be configured to:

receive, via input module 126, an exercise type 14. Exercise type 14 may be input by user 110, for example;

capture, via video capture device 120, a video 16 of user 110 performing one or more reps 18 of exercise type 14;

retrieve, via memory module 124, rep detection model 10' corresponding to exercise type 14. A particular rep detection model 10' corresponding to exercise type 14 may be selected from among a plurality of rep detection models 10 for various exercise types;

execute rep detection model 10' to identify rep(s) 18 in video 16;

retrieve, via memory module 124, one or more error indication models 12' corresponding to exercise type 14, each error indication model 12' corresponding to a particular error type 38' corresponding to exercise type 14. Particular error indication models 12' and particular error types 38' corresponding to exercise type 14 may be selected from among a plurality of error indication models 12 and a plurality of error types corresponding for various exercise types;

for each error indication models 12', execute error indication model 12' to generate error indication 20 for each rep 18; and output, via output module 128, feedback 21 to user 110 based on one or more error indications 20.

In some embodiments, feedback 21 may include, without limitation, suitable indication(s) of the presence or absence of form errors in each rep 18 in user video 16, indications of the times and/or frames of user video 16 that contain the form errors, instructions for correcting one or more form errors that may be present in user video 16 and/or the like.

In some embodiments, memory module 124 stores exercise classification model 22. Exercise classification model 22 receives as input a video 16 of a user performing one or more exercise reps 18 and outputs an exercise type label 24 corresponding to the exercise type of the exercise reps 18. Exercise classification model 122 may output an exercise label 24 for video 16 (e.g. as a whole) or for each rep 18 identified in video 16. Where memory module 124 stores exercise classification model 22, processor 122 may be configured to:

retrieve, via memory module 124, exercise classification model 22; and execute exercise classification model 22 to generate exercise type label 24 of video 16.

Exercise type label 24 may be used to confirm exercise type 14 received by input module 126. In some embodiments, processor 122 may be configured to generate exercise type label 24 instead of receiving exercise type 14. In such embodiments, processor 122 may be configured to use exercise type label 24 in the place of exercise type 14 for functionality described elsewhere herein. For example, processor 122 may retrieve rep detection model 10' (from among a plurality of rep detection models 10 corresponding to various exercise types) and error indication model 12' (from among a plurality of error indication models 12 corresponding to various exercise types) based on exercise type label 24 instead of a received exercise type 14. Except where clearly indicated by the description or by the context, exercise type 14 is used in the remainder of this without loss of generality.

In some embodiments, memory module 124 stores feedback 21 comprising pre-recorded audio and/or visual media. The media may include messages and/or instructions to be played for user 110. The messages may include one or more of: directions on using system 100, directions on performing a rep of exercise of type 14, corrective instructions for remedying a form error in a rep 18 of exercise of type 14, and/or encouraging messages.

In some embodiments, one or more of video capture device 120, processor 122, memory module 124, input module 126, and output module 128 may be provided by separate devices, and communicatively coupled by a wired or wireless interface, for example: USB, Ethernet, WiFi, Bluetooth, or a cellular network (i.e. 3 g, 4 g, etc.).

Figure 1B:
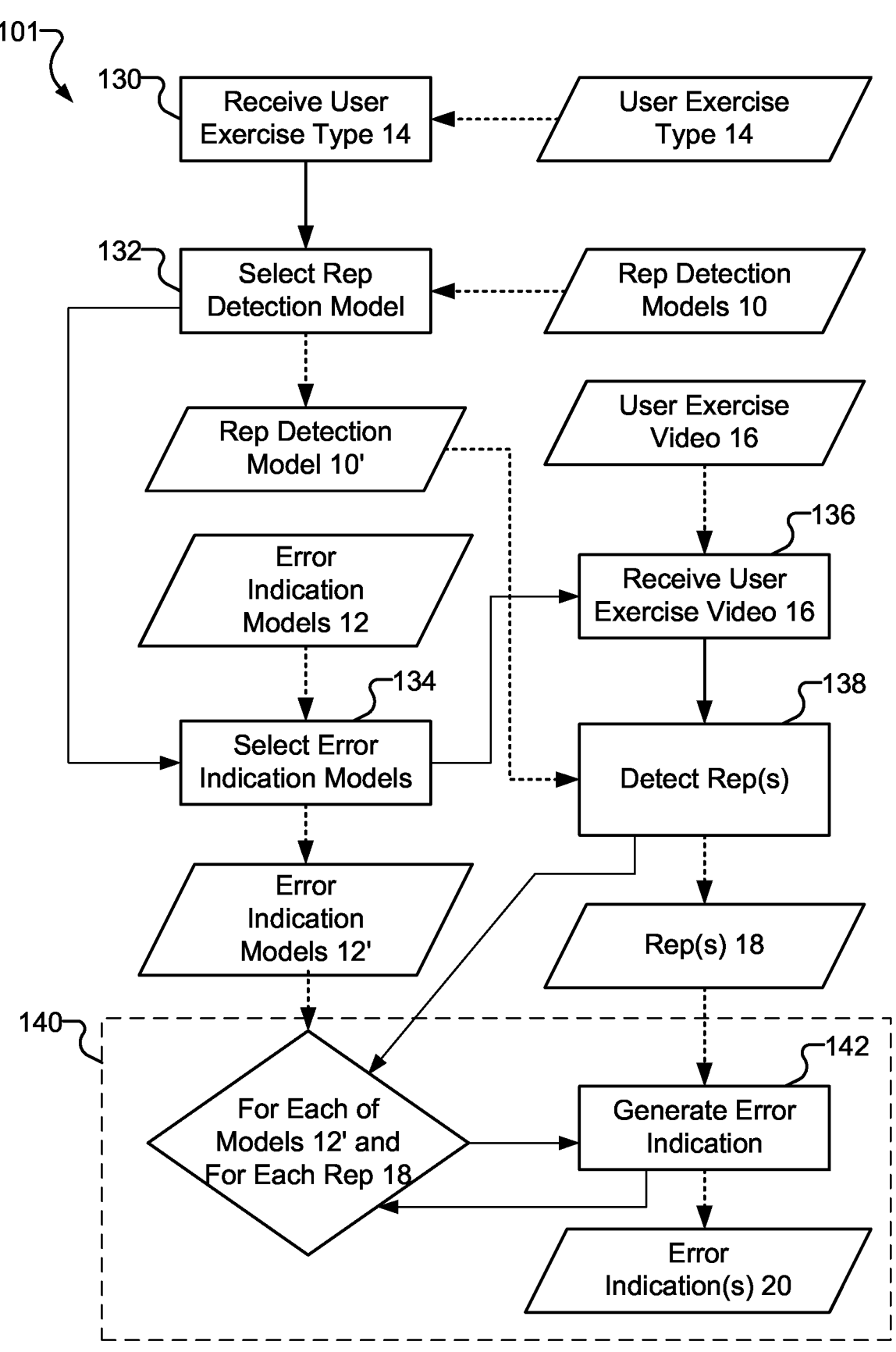
FIG. 1B depicts an exemplary method for detecting potential problems (e.g. form errors) of a user performing a physical exercise, according to one embodiment of the present invention.

FIG. 1B depicts method 101 for detecting one or more form errors of user 110 performing a rep 18 of an exercise type 14, according to one embodiment of the present invention. Method 101 may be performed by system 100. In the FIG. 1B illustration, solid lines with arrows are indicative of process flow, while dotted lines with arrows are indicative of data flow.

Step 130 of method 101 comprises receiving (or otherwise obtaining) a user exercise type 14. Exercise type 14 indicates a type of exercise, for example: back squat, shoulder press, push-up, pull-up and/or the like. Exercise type 14 may be input or otherwise provided by user 110, for example by user 110 selecting an exercise type 14 from among a variety of exercise types, keying in an exercise type 14 and/or the like. Exercise type 14 may be generated from user video 16 as part of step 130, for example by using exercise classification model 122 discussed above, which outputs an exercise type label 24 which can be used as exercise type 14 for subsequent processing.

Step 132 of method 101 comprises selecting a rep detection model 10' from among a plurality of detection models 10 (e.g. a database of rep detection models 10) corresponding to various exercise types. Each of rep detection models 10 corresponds to an exercise type. Step 132 comprises selecting rep detection model 10' which corresponds to exercise type 14.

Step 134 of method 101 comprises selecting one or more error indication models 12' from among a plurality of error indication models 12 (e.g. a database of error detection models 12) corresponding to various exercise types. Each of error indication models 12 corresponds to an exercise type. Step 134 comprises selecting one or more error indication models 12' corresponding to exercise type 14.

Each of the one or more error detection models 12' selected in step 134 corresponds to a different error type 38' for exercise type 14 with a one to one correspondence between error types 38' and error detection models 12'. For example, where exercise type 14 is "back squat", the error indication models 12' selected in step 134 corresponding to exercise type "back squat" may include "incorrect foot position", "incorrect bar position", "chest insufficiently upright" and/or "incorrect knee position". Each of "incorrect foot position", "incorrect bar position", "chest insufficiently upright" and/or "incorrect knee position" may be an error type 38' corresponding to the exercise type "back squat" and each of the step 134 error detection models 12' may correspond to one of these error types 38'.

In some embodiments, method 101 may be performed only for a particular exercise type 14 (e.g. for a back squat). In some such embodiments, steps 130, 132 and 134 may not be required, as the exercise type 14 is given, rep detection model 10' need not be selected (since it may be hard-coded for the particular exercise type 14) and error indication models 12' need not be selected (since they may be hard-coded for the particular exercise type 14).

From step 134, method 101 proceeds to step 136, which comprises receiving video 16 of user 110 performing one or more reps 18 of exercise type 14. As discussed elsewhere herein, video 16 may be captured by any suitable image-capture apparatus and received at system 100 by any suitable technique. In one exemplary embodiment, video 16 is captured on the mobile phone of user 110 and some or all of system 100 and method 101 are implemented by the same mobile phone.

In some embodiments, step 136 comprises formatting user video 16. Formatting user video 16 may comprise cropping video 16 to a desired perspective. Formatting user video 16 may comprise adding pixels to the frames of video 16 to generate frames of a desired perspective. A desired perspective may be a horizontal to vertical pixel ratio of 1×1, 6×4, or 4×6 pixels.

Method 101 then proceeds to step 138 which comprises detecting one or more rep(s) 18 in video 16 using the step 132 rep detection model 10'. Rep detection step 138 is described in more detail below.

Method 101 then enters a loop 140, which comprises performing step 142 for each step 134 error indication model 12' and for each rep 18 detected in step 138. Step 142 comprises generating error indication 20 of the current rep 18 using the current error indication model 12". Error indication 20 may indicate a probability that an error of the type of the current error indication model 12' is present in the current rep 18.

Figure 2A:
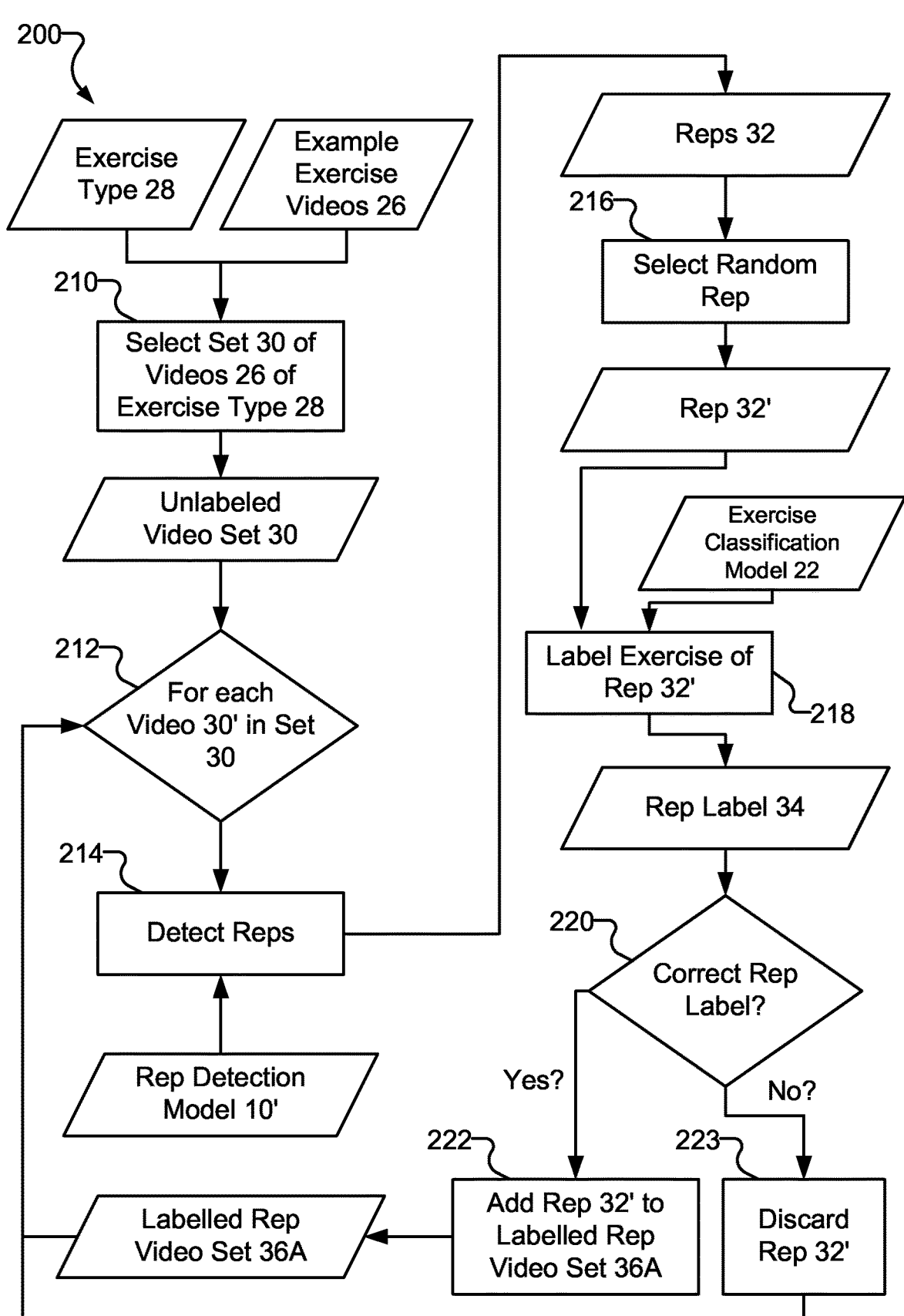
FIGS. 2A and 2B depict an exemplary method for generating training data for training a form error detection model, according to one embodiment of the present invention.
Figure 2B:
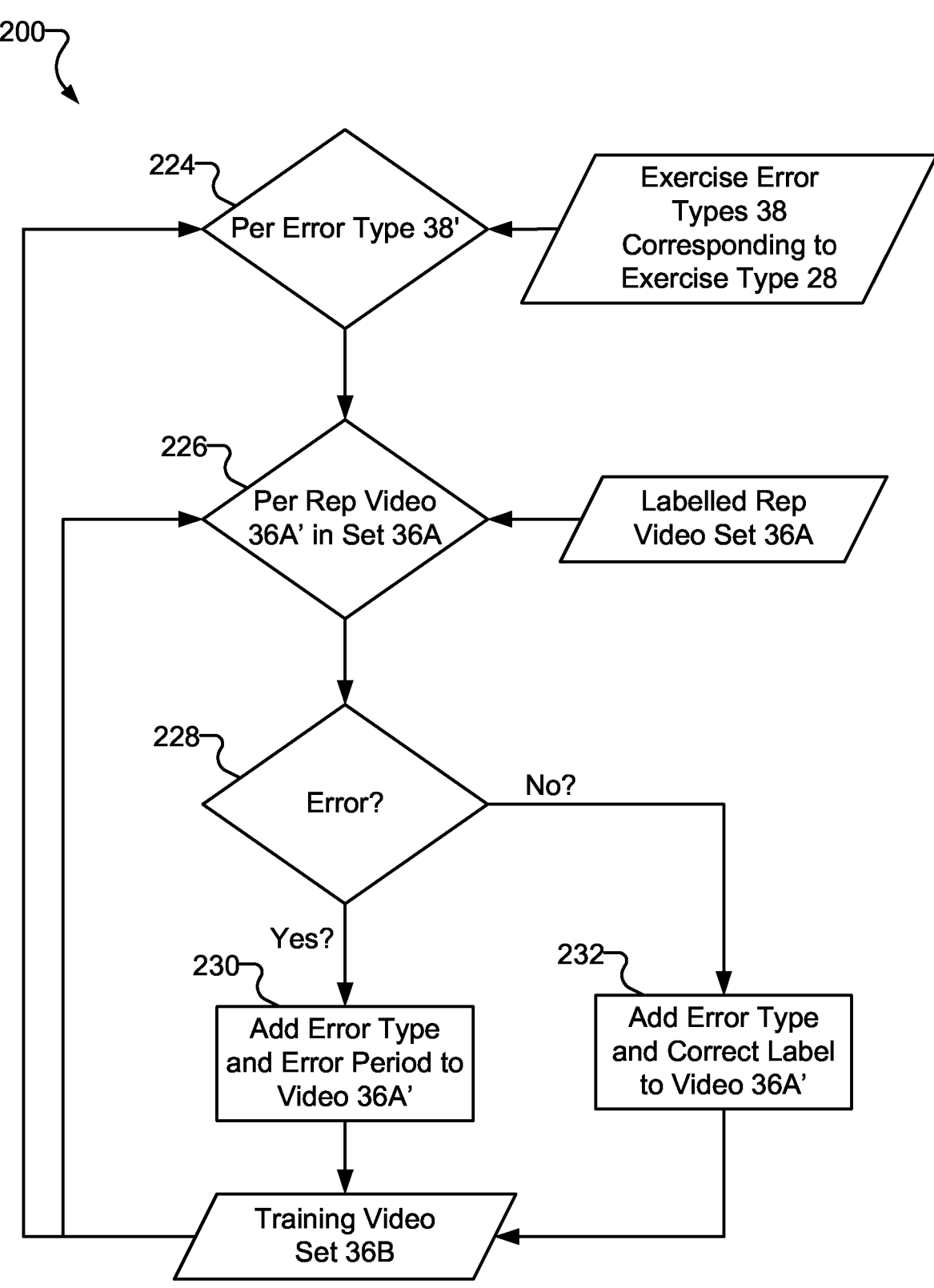

FIGS. 2A to 2B depict method 200 for generating training data for training one or more error indication models 12 for an exercise type 28, according to an example embodiment.

Method 200 starts in step 210 which comprises selecting a set 30 of example exercise videos 26 of an exercise type corresponding to exercise type 28. Exercise type 28 is the type of exercise for which method 200 will generate training data. Each of videos 26 comprises a plurality of numbered frames.

Example exercise videos 26 may comprise videos stored on the internet, for example on a social media platform such as Instagram™, YouTube™, Facebook™ and/or the like. Selecting set 30 may comprise downloading a set of social media videos 26 associated with exercise type 28. For example, Instagram™ videos may be associated with a text tag used to describe the contents of the video. Selecting set 30 in step 210 may comprise searching the tags of Instagram™ videos for text generally matching exercise type 28. For example, if exercise type 28 is "back squat", then step 210 may comprise searching Instagram™ for videos associated with tags containing the text "back squat", or some variation thereof, such as the text "backsquat", "squat" or "bsquat".

Method 200 then proceeds to a loop 212 which comprises performing steps 214 to 222 of method 200 for each video 30' in set 30.

Step 214 of method 200 comprises detecting one or more reps 32 of exercise type 28 in video 30' using a rep detection model 10' corresponding to exercise type 28. Rep detection step 214 is described in more detail below.

Method 200 then proceeds to step 216, which comprises randomly selecting one rep 32' from among the reps 32 detected in step 214. A rep 32' may be randomly selected from among the step 214 reps 32 by assigning each of the step 214 reps 32 an index number, and generating a random one of the index numbers.

Method 200 then proceeds to step 218 which comprises classifying rep 32' using exercise classification model 22 to generate rep label 34. Exercise classification model 22 may comprise any suitable model that can classify video clips showing exercise reps (e.g. rep 32') into exercise types (e.g. rep label 34).

For example, in one particular embodiment, exercise classification model 22 comprises a 3D spatio-temporal convolutional neural network trained, using supervised machine learning based on the stochastic gradient descent machine learning technique, with video clips showing exercise reps pre-labelled with a particular exercise type. During training, exercise classification model 22 is rewarded if it is able to correctly identify/label the exercise type (according to the pre-labelled exercise type) in a rep shown in a training video clip and is penalized if it incorrectly identifies/labels the exercise type (according to the pre-labelled exercise type) in a rep shown in a training video clip. After sufficient training using pre-labelled training video clips showing various exercises labelled with their corresponding exercise type, the neural network (exercise classification model 22) is able to infer the exercise type in any video clip showing an exercise rep (e.g. rep 32'). The output of step 218 is a rep label 34 corresponding to the block 216 randomly selected rep 32'. It will be appreciated that other forms of neural networks could be used to implement classification model 22 and/or other techniques for supervised or unsupervised machine learning based training could be used to train classification model 22 provided that exercise classification model 22 (once properly trained) is able to receive, as input, video comprising one or more reps (e.g. rep 32') and classify or label such reps as belonging to a particular exercise type (e.g. outputting rep label 34).

Method 200 then proceeds to block 220 which comprises comparing the block 218 rep label 34 to the input exercise type 28 to verify whether the randomly selected rep 32' is indeed of the same exercise type as the input exercise type 28. If rep label 34 matches exercise type 28, then rep 32' is a rep of exercise type 28, and rep 32' is added to labelled rep video set 36A in step 222. If rep label 34 does not match exercise type 28, then rep 32' is not a rep of exercise type 28, and rep 32' is discarded.

In some embodiments, rep label 34 generated by exercise classification model 22 may comprise an exercise type, and a confidence probability. Where rep label 34 comprises a confidence probability, step 220 may comprise discarding rep 32' if the confidence probability of rep label 34 is below a threshold, for example 50% (in some embodiments) or 75% (in some embodiments).

Steps 218 and 220 may be considered a verification step in the sense that they involve verifying whether randomly selected rep 32' from a particular video 30' corresponds to the input exercise type 28. In some embodiments, these verification steps can be performed on a video prior to randomly selecting a rep. Instead, a larger portion of a particular video 30' (perhaps comprising several reps) may be verified and exercise classification model 22 may be capable of labelling a video comprising several reps. In such embodiments, a single rep 32' may be randomly selected and added to labelled rep video set 36A after its corresponding video 30' has been verified to comprise one or more reps of the input exercise type 28.

Upon the completion of the loop 212 (i.e. after processing all of videos 30' in set 30), the output of loop 212 is labelled rep video set 36A comprising a number of randomly selected reps 32' from a corresponding number of videos 30, where each rep 32 has been verified to be of the same exercise type as input exercise type 28. Method 200 then proceeds to loop 224 (FIG. 2B). Loop 224 comprises performing steps 226 to 232 for each error type 38' from among a set of exercise error types 38 which correspond to the input exercise type 28. The set of exercise error types 38 may comprise individual error types 38' each of which corresponds to a possible form error corresponding to input exercise type 28. For example, where exercise type 28 is "back squat", the set of exercise error types 38 may include individual error types 38' such as "incorrect foot position", "incorrect bar position", "chest insufficiently upright", "incorrect knee position" and/or the like. It will be appreciated that if the input exercise type 28 is different, the set of exercise error types 38 and the individual error types will be different. Furthermore, the number of error types 38' in each set of exercise error types 38 may be different for each input exercise. For example, where input exercise 28 is a push up, the set of exercise error types 38 may include individual error types 38' such as "incorrect hand placement", "bum too high" and/or the like.

Method 200 then proceeds to loop 226 which involves performing steps 228 to 232 for each rep video 36A' in labelled rep video set 36A.

Step 228 of method 200 comprises reviewing the current rep video 36A' for an error of the current error type 38'. If current rep video 36A' contains an error of current error type 38', then method 200 proceeds to step 230. If rep video 36A' does not contain an error of current error type 38', then method 200 proceeds to step 232. Step 230 of method 200 comprises adding an error type label 40' and an associated error period label 42' to current rep video 36A' (e.g. as metadata attached to current rep video 36A' or as separate fields in a data structure corresponding to current rep video 36A'). The error type label 40' assigned in step 230 corresponds to current error type 38'. Error period label 42' may indicate an error start frame (or error start time) and an error end frame (or error end time) between which an error of current error type 38' occurs. Step 232 comprises adding an error type label 40' corresponding to current error type 38' and a "correct" label to current rep video 36A' (e.g. as metadata attached to current rep video 36A' or as separate fields in a data structure corresponding to current rep video 36A').

The error identification and labelling procedures of steps 228, 230 and 232 may be performed in part by a human expert (e.g. someone with experience identifying errors in exercises). Specifically, a human expert may identify the existence or non-existence of an error of the current error type 38' and the start/end frames/times of that error within the current rep video 36A' (as part of block 228) and may input this information to facilitate the performance of steps 230 or 232.

The output of method 200 (at the conclusion of loops 226 and 224) is a training video set 36B. Training video set 36B comprises labelled rep video set 36A once steps 224 to 232 have been performed for each of error types 38 corresponding to input exercise type 28 and for each video in set 36A. More specifically, training video set 36B comprises a set of videos of single reps that have been verified to be of input exercise type 28 wherein each rep video has been labelled with whether it contains any of exercise error types 38 (corresponding to the input exercise type 28) and, for each error type 38' from among the set of exercise error types 38, the start frame/time and end frame/time of that error type 38'. It will be appreciated from the above discussion of training data preparation that method 200 may be performed to generate a training video set 36B for each exercise type that could be considered by system 100 (FIG. 1A) or method 101 (FIG. 1B) and that each such exercise type would be an input exercise type 28 to method 200. That is, training video set 36B may be prepared (using method 200) for each exercise type that could be considered by system 100 (FIG. 1A) or method 101 (FIG. 1B).

Figure 3:
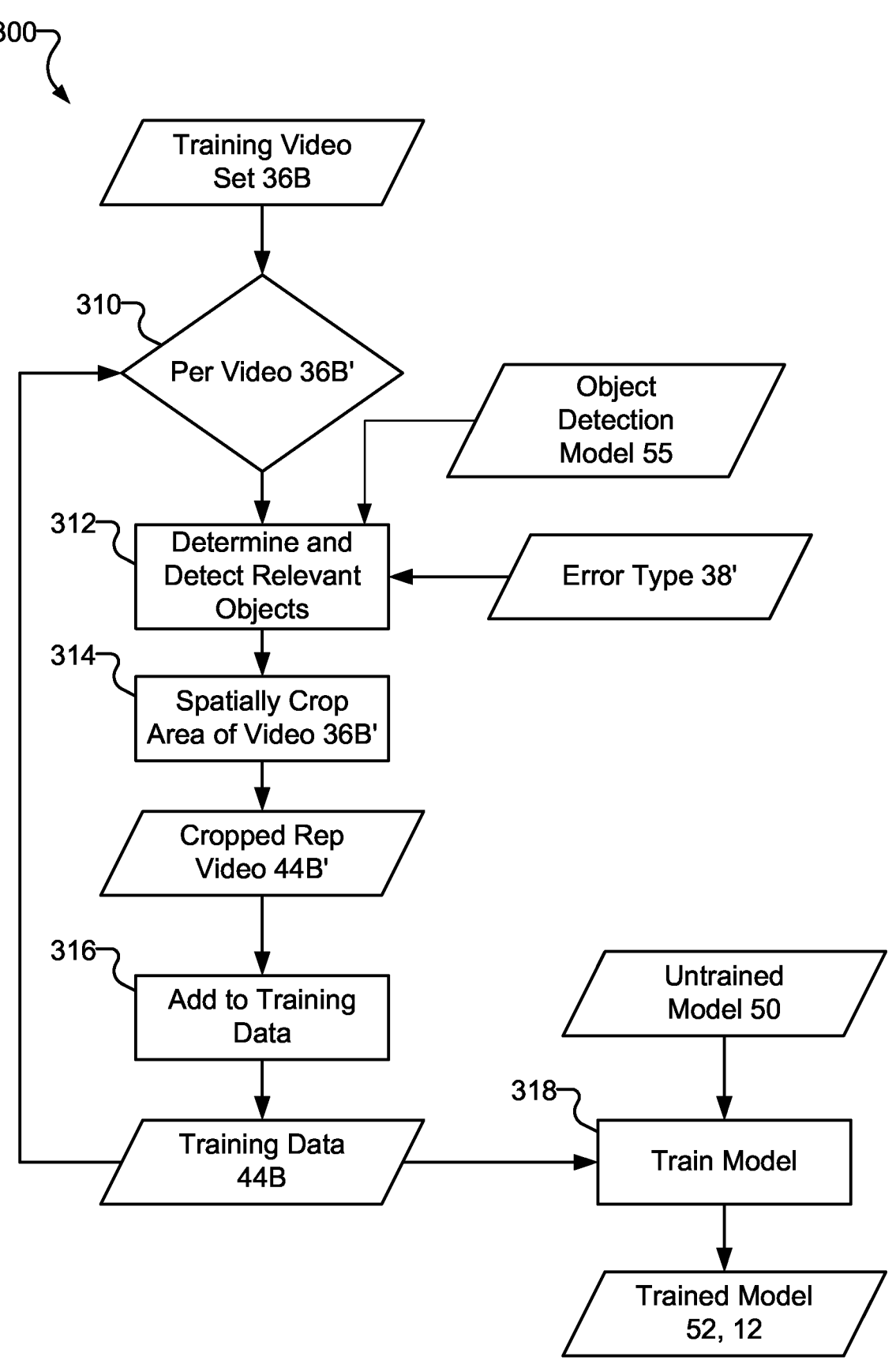
FIG. 3 depicts an exemplary method for training an error detection model according to one embodiment of the present invention.

FIG. 3 depicts method 300 for training an error indication model 52 according to one embodiment of the present invention. Error indication model 52 trained according to method 300 may be used as one of error indication models 12 in system 100 (FIG. 1A) and/or method 101 (FIG. 1B). Method 300 may train error indication model 52 using training data (e.g. training video set 36B) prepared according to method 200 (FIGS. 2A, 2B). Method 300 trains an error indication model 52 to identify a particular error type 38' corresponding to an exercise type. For example, method 300 may be used to train an error indication model 52 for determining a probability of a "foot position" error (i.e. a particular error type 38') corresponding to a "back squat" (an exercise type). The error indication models 52 trained in method 300 may provide the error indication models 12 of system 100 (FIG. 1A) and method 101 (FIG. 1A). The particular error type 38' in method 300 may correspond one of the error types 38' in method 200 (FIG. 2B). Method 300 may be performed once for each error type 38' (an input error type 38') to generate an error indication model 52 capable of identifying that error type 38'. As discussed elsewhere herein, each exercise type 38' may be one of a set of exercise error types 38, all of which correspond to a particular exercise type. Thus, if system 100 (FIG. 1A) and method 101 (FIG. 1B) are to be used for multiple exercise types, then method 300 may be performed for each input error type 38' for among each set of exercise error types 38 for each exercise type. Each error indication model 52 trained using method 300 generates one error indication model 12 (FIGS. 1A, 1B) capable of identifying a particular error type 38' (i.e. the input error type 38' to method 300).

Method receives (as input) training video set 36B (e.g. the output of training data preparation method 200) for a particular exercise type and an error type 38' from among the set of error types 38 corresponding to the particular exercise type. Method 300 comprises a loop 310 which involves performing steps 312 to 316 for each rep video 36B' in training video set 36B.

Step 312 of method 300 comprises determining and detecting one or more relevant objects in video 36B' that are relevant to input error type 38'. Such relevant objects may include parts of a body, parts of the environment and/or parts of exercise equipment. Such objects may be referred to as objects of interest for the purposes of method 300. For example, if input error type 38' is "foot position" for a "back squat" exercise type, then the relevant objects of interest determined and detected in video 36B' as part of step 312 may comprise the feet of the person performing the exercise in video 36B'. As another example, if input error type 38' is "insufficient arm flexion" for a pull up exercise type, then the relevant objects of interest determined and detected in video 36B' as part of step 312 may comprise the chest of the person performing the exercise in video 36B' and the pull up bar shown in video 36B'.

Step 312 may be performed using an object detection model 55. For example, step 312 may be performed using an object detection model 55 based on a 3D spatio-temporal convolutional neural network backbone which is able to segment (e.g. identify boundaries of or bounding boxes around) different objects (e.g. on a per-frame basis). This backbone may then be trained, using supervised machine learning based on the stochastic gradient descent machine learning technique, with video clips showing pre-labelled objects (e.g. parts of moving human bodies), exercise equipment or objects (e.g. barbells, dumbbells, exercise machines and/or the like). During training, object detection model 55 may be rewarded if it is able to correctly identify/label objects (according to the pre-labelled objects) in a rep shown in a training video clip and may be penalized if it incorrectly identifies/labels objects (according to the pre-labelled objects) in a rep shown in a training video clip. After sufficient training using pre-labelled training video clips showing various pre-labelled objects, the neural network (object detection model 55) is able to segment different objects (on a per-frame basis) and to infer the types of such objects in any video clip showing an exercise rep (e.g. rep video 36B'). The output of step 312 may comprise locations (on a per-frame basis) and labels for different objects of interest that are relevant to error type 38' in rep video 36B'. The locations of objects of interest (on a per-frame basis) may be identified using one or more bounding boxes. It will be appreciated that other forms of neural networks could be used to implement object detection model 55 and/or other techniques for supervised or unsupervised machine learning based training could be used to train object detection model 55 provided that object detection model 55 (once properly trained) is able to receive, as input, video comprising one or more reps (e.g. rep video 36B') and is able to identify the locations of different objects of interest (on a per-frame basis) and to infer the types of such objects of interest in any video clip showing an exercise rep (e.g. rep video 36B').

Method 300 then proceeds to step 314 which comprises spatially cropping the frames of video 36B' to a smaller portion of the original frames that still contains the step 312 objects of interest. Step 314 may comprise determining a cropping region, wherein the cropping region is a region in each frame of video 36B' which contains all bounding boxes identified as belong to any objects of interest in any frame in video 36B'. The step 314 process of spatially cropping video 36B' generates cropped rep video 44B'.

Step 316 of method 300 comprises adding cropped rep video 44B' to training data 44B. As part of block 314 or 316, the cropped rep video 44B' may be up-sampled or down-sampled using any suitable technique and may be padded with grey pixels, so that all cropped rep videos 44B' that are added to training data 44B in step 316 have the same number of pixels and the same aspect ratio.

After the completion of loop 310, method 300 has generated training data 44B which comprises a set of individual cropped rep videos 44B' labelled with the presence, start time/frame and end time/frame of a particular error type 38' and cropped to a region corresponding to objects of interest for that particular error type 38'.

Method 300 then proceeds to step 318 which comprises training untrained model 50 using training data 44B to generate trained model 52.

As discussed elsewhere herein, trained model 52 may then be used as one of error indication models 12 in system 100 depicted in FIG. 1A, and/or in method 101 depicted in FIG. 1B.

Error identification model 52 trained in block 318 may comprise a 3D spatio-temporal convolutional neural network backbone and may be trained, using supervised machine learning based on the stochastic gradient descent machine learning technique, with training data 44B which comprises comprises a set of individual cropped rep videos 44B' each of which is labelled (on a frame-by-frame basis) with the presence of a particular error type 38' and cropped to a region corresponding to objects of interest for that particular error type 38'. During training, error identification model 52 may be rewarded if it is able to correctly identify/label frames where error type 38' is present (or absent) and is penalized if it incorrectly identifies/labels the presence (or absence) of error type 38' (according to the pre-labelled training data 44B. After sufficient training using training data 44B, the neural network (error identification model 52) is able to infer the presence or absence of error type 38' in the frames of any video clip showing an exercise rep (e.g. rep 18—see FIG. 1B).

The output of step 318 is a trained error identification model 52 which is able to receive, as input, a video comprising one or more reps of an exercise type (for example, reps 18 of exercise type 14) shown in method 101 (FIG. 1B) and to infer the presence (or absence) of a particular error type 38' that is relevant to the exercise type 14. As discussed elsewhere herein, trained error identification model 52 may be used as one of error identification models 12 in system 100 (FIG. 1A) and/or method 101 (FIG. 1B). It will be appreciated that other forms of neural networks could be used to implement error identification model 52 and/or other techniques for supervised or unsupervised machine learning based training could be used to train error identification model 52, provided that error identification model 52 (once properly trained) is able to receive, as input, video comprising one or more reps (e.g. reps 18) of a particular exercise type (e.g. exercise type 14) and to identify (e.g. on a frame-by-frame basis) the presence or absence of an error type 38' within the input video.

In some embodiments, once trained, the inference aspect of the neural network used in error identification model 52 may output a probability p (e.g. where $0<=p<=1$) of an error of error type 38' being present in a particular frame of an input video. In some such embodiments, additional logic may be used to binarize the conclusion that an error is present (or absent) in the frames of an input video. By way of simple example, if for a particular frame of input video, $p>p_{thresh}$, then error identification model 52 may conclude that an error is present in that frame and may conclude that an error is absent from that frame for any other value of p. The value of $p_{thresh}$ may be a configurable parameter, depending on whether the system is configured to be more sensitive to false positive results or false negative results. In some embodiments, error identification model 52 may conclude that an error is present if a number n of consecutive frames with $p>p_{thresh}$ is greater than a threshold (i.e. $n>n_{thresh}$). The value of $n_{thresh}$ may be a configurable parameter, which may depend on whether the system is configured to be more sensitive to false positive results or false negative results and whether the system is configured to be sensitive or insensitive to short temporal periods of fluctuation (e.g. noise). In some embodiments, a moving average filter is applied to a window of length x frames. In some such embodiments, error identification model 52 may conclude that an error is present if the average probability ($p_{av}$) of the preceding x frames is greater than $p_{thresh}$ (ie $p_{av}>p_{thresh}$) The value of x may be a configurable parameter which may depend on whether the system is configured to be more sensitive to false positive results or false negative results and whether the system is configured to be sensitive or insensitive to short temporal periods of fluctuation (e.g. noise). It will be appreciated from this discussion that there are a number of suitable techniques that could be used alone and/or in combination to binarize the output of the inference portion of error identification model 52.

Figure 4A:
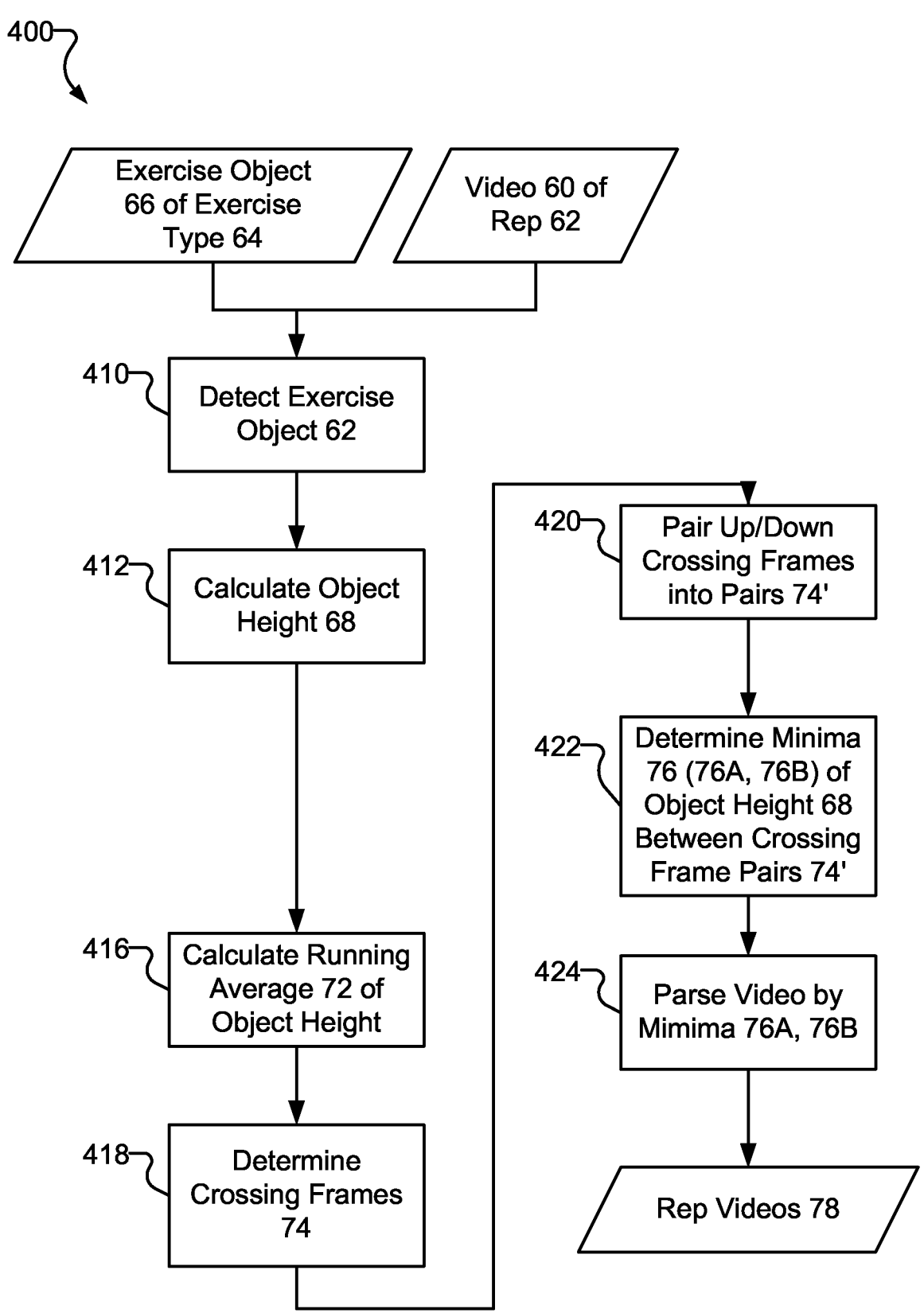
FIGS. 4A and 4B depict an exemplary method for detecting an exercise repetition (rep) within a video of a person performing a physical exercise, according to one embodiment of the present invention.
Figure 4B:
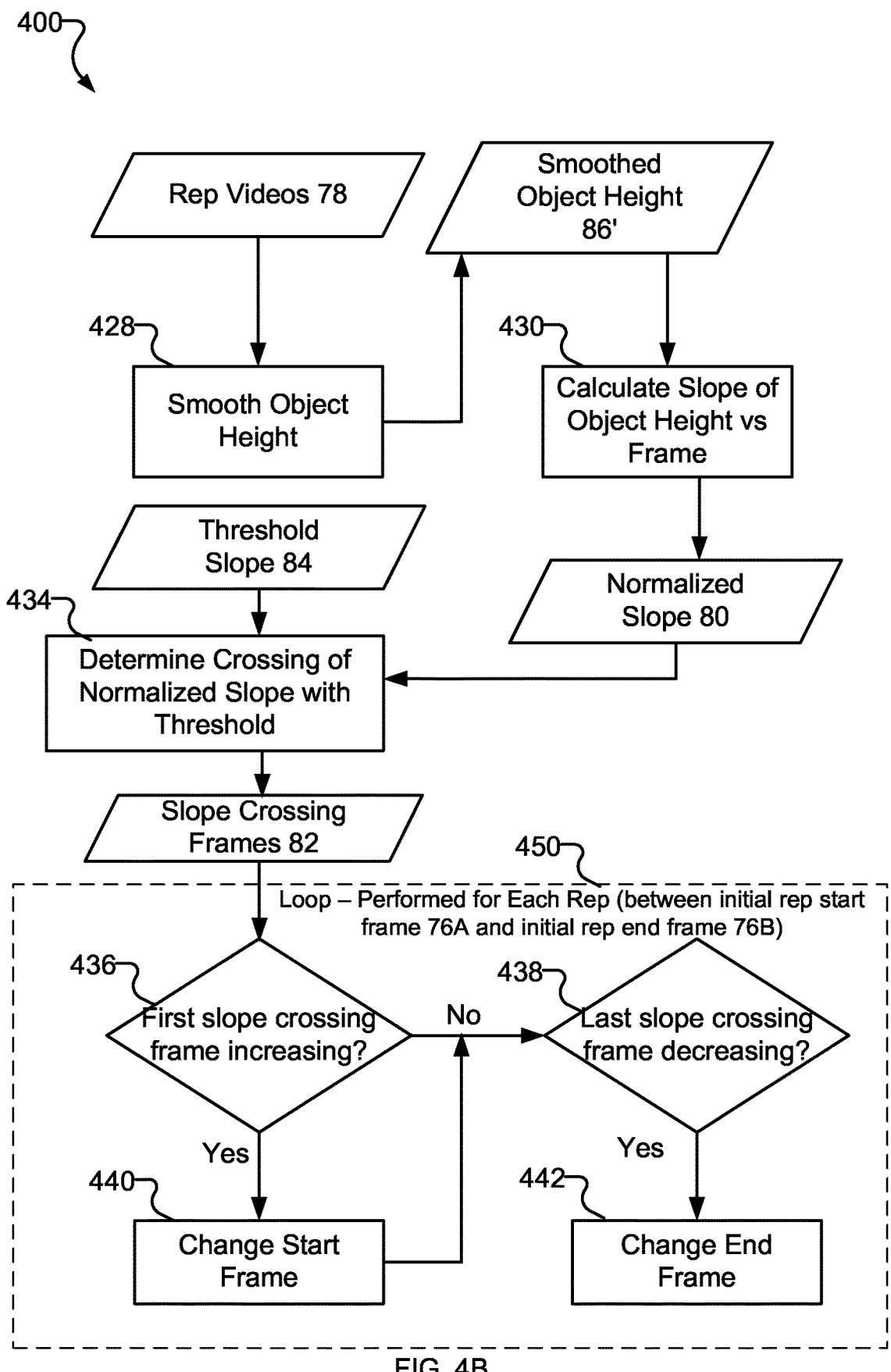

FIGS. 4A and 4B depict method 400 for generating a rep start frame and a rep end frame for an exercise rep in a video of an individual performing one or more exercise reps. That is, method 400 may be used to parse input video into individual reps (identify the start frame and stop frame of individual reps) within the input video. Method 400 may be used to implement rep detection models 10 of system 100 (FIG. 1A) or method 101 (FIG. 1B) and/or to perform step 138 of method 101 (FIG. 1B). Method 400 may be additionally or alternatively used to perform block 214 of method 200 (FIG. 2A).

Method 400 start in block 410 and receives, as input, video 60 showing one or more reps 62 of an exercise type 64. In the illustrated embodiment, step 410 also receives, as input, one or more exercise objects 66 that are relevant to exercise type 64. In practice, any computer system (e.g. system 100) or processor (e.g. processor 122) implementing method 400 may have access (via memory module 124 or otherwise) to the one or more exercise objects 66 that are relevant for rep detection in relation to exercise type 64. Exercise objects 66 may comprise parts of a human body (e.g. a person's shoulders or arms) and/or the parts of exercise equipment (e.g. barbell, dumbbell(s), pull up bar, exercise machines and/or the like). Step 410 of method 400 comprises identifying one or more exercise objects 66 in each frame of video 60 or determining that the exercise object 66 is not present in a particular frame. Video 60 comprises a sequence of video frames of an individual performing at least one rep 62 of a physical exercise of exercise type 64. Exercise object 66 is a visually recognizable object in video 60. The movement of object 66 between frames of video 60 allows method 400 to detect a rep start frame and a rep end frame of rep 62.

Exercise object 66 is associated with an exercise type 64. For example, where exercise type 64 is "back squat", exercise object 66 may comprise a visual representation of a barbell.

Step 410 comprises identifying an object region in each frame of video 60 containing exercise object 66. In some embodiments, step 410 comprises generating a bounding box in each frame of video 60 containing object 66. Step 410 may be accomplished using an object detection model that is the same or similar to object model 55 (FIG. 3) discussed elsewhere herein. Step 410 may involve steps that are the same or similar to those of block 312 (FIG. 3) discussed elsewhere herein. In some embodiments, as part of block 410, input video 60 may be temporally cropped at the beginning and end of the video based on the presence or absence of exercise objects (e.g. exercise objects 66) and/or based on the lack of movement of exercise objects 66. For example, in the case of the back squat, block 410 may comprise temporally cropping input video 60 at the beginning or end where the person performing the exercise and the barbell are not both detected in the same video frame and/or where the barbell is not moving significantly between frames at or near its minimum position (e.g. within a threshold distance from its minimum position).

Step 412 of method 400 comprises calculating an object height 68 for each frame of video 60 based on the object region in each frame. Where step 410 comprises generating a bounding box, object height 68 may be the average height of the bounding box in each frame, the height of one edge (e.g. the bottom edge or top edge) of the bounding box in each frame, or the height of one extremum (e.g. the bottom extremum or top extremum) of the bounding box in each frame.

Step 416 of method 400 comprises determining a running average 72 of the step 412 object height 68 versus frame number. For example, running average 72 may represent the average object height 68 for the previous x number of frames. The parameter x which specifies the number of frames in the step 416 moving average may comprise a configurable parameter.

Step 418 of method 400 comprises determining one or more "crossing" frames 74 wherein object height 68 crosses over the running average 72 for the frame. In some cases, step 418 determines a crossing frame 74 when object height 68 is equal to the running average 72. It will be appreciated that there may not be a particular frame where object height 68 is exactly "equal" to the running average 72. Step 418 may, in some cases, determine a crossing frame 74 when object height 68 is higher than running average 72 in a first frame and then lower than running average in a second, immediately subsequent frame. In some such instances, step 418 may determine the one of the first and second frames where object height 68 is closest to the moving average 72 to be the crossing frame 74. Step 418 may, in some cases, determine a crossing frame 74 when object height 68 is lower than running average 72 in a first frame and then higher than running average in a second, immediately subsequent frame. In some such instances, step 418 may deter-mine the one of the first and second frames where object height 68 is closest to the moving average 72 to be the crossing frame 74. In some cases, step 418 may determine a crossing frame 74 when object height 68 is sufficiently close to (e.g. within a threshold distance) moving average 72.

Each of crossing frames 74 identified in step 418 is either an "up-crossing" frame, or a "down-crossing" frame. An up-crossing frame 74 is a crossing frame where object height 68 is increasing when object height 68 crosses running average 72. A down-crossing frame is a crossing frame where object height 68 is decreasing when object height 68 crosses running average 72. An up-crossing frame 74 may be determined by identifying a frame with an object height 68 greater than or equal to the running average 72 for the frame and which follows a frame with an object height 68 less than the running average 72 for the frame. A down-crossing frame 74 may be determined by identifying a frame with an object height less than or equal to the running average 72 for the frame and which follows a frame with an object height 68 greater than the running average 72 for the frame.

Step 420 of method 400 comprises pairing increasing and decreasing crossing frame 74 into crossing frame pairs 74'. For some exercise types (such as the back squat), crossing frame pairs 74' may comprise an up-crossing frame 74 followed by a subsequent and temporally adjacent down-crossing frame 74. For some exercise types (such as the pull up), crossing frame pairs 74' may comprise a down-crossing frame 74 followed by a subsequent and temporally adjacent up-crossing frame 74. In the remainder of this description, unless the description or context clearly dictates otherwise, it will be assume (without loss of generality) that a crossing frame pair 74' comprises an up-crossing frame 74 followed by a subsequent and temporally adjacent down-crossing frame 74.

Step 422 of method 400 comprises, for each step 420 crossing frame pair 74', determining a minimum frame 76 (where object height 68 is a minimum) that precedes (temporally) the first crossing frame 74 in the crossing frame pair 74' and a minimum frame 76 (where object height 68 is a minimum) that follows (temporally) the second crossing frame 74 in the crossing frame pair 74'. The minimum frame 76 (where object height 68 is a minimum) that precedes (temporally) the first crossing frame 74 in the crossing frame pair 74' may be referred to as the preceding minimum frame 76A and the minimum frame 76 (where object height 68 is a minimum) that follows (temporally) the second crossing frame 74 in the crossing frame pair 74' may be referred to as the succeeding minimum frame 76B. It will be understood from the description herein that where a crossing frame pair 74' comprises a down-crossing frame 74 followed by a subsequent and temporally adjacent up-crossing frame 74 (e.g. in the case of a pull up), step 422 may detect a preceding maximum frame and a succeeding maximum frame.

Step 424 of method 400 comprises generating a rep start frame which comprises the step 422 preceding minimum frame 76A and a rep end frame which comprises the step 422 succeeding minimum frame 76B. Step 424 may comprise temporally cropping video 60 to keep only the portion of the video between each rep start frame 76A and each subsequent rep end frame 76B and discarding other parts of the video that is not between a pair of rep start and end frames 76A, 76B. The output of step 424 is rep video 78.

Method 400 then continues to step 428 (FIG. 4B) which comprises smoothing object height 68 for each frame of rep video 78 to generate smoothed object height 68'. Smoothing object height 68 for each frame may comprise applying a moving average filter which averages the object height 68 for each frame with the object height 68 of a number x of previous frames. The number x of frames taken into the moving average filter is a configurable parameter of method 400. In one example, step 428 involves a moving average filter of length x=9 previous frames.

Step 430 of method 400 comprises calculating the absolute value of the normalized slope (absolute value of the normalized time-derivative or frame-derivative) 80 of smoothed height 68'. For brevity, unless the description or the context clearly indicates otherwise, the absolute value of the normalized slope 80 may be referred to herein as the normalized slope 80 or the slope 80. Normalized slope 80 may be determined, for each frame, by determining a difference between the smoothed height 68' of the current frame and the smoothed height 68' of the preceding frame, divided by the difference between the maximum smoothed height 68' and minimum smoothed height 68' of rep video 78.

Step 434 of method 400 comprises determining one or more slope crossing frames 82 where normalized slope 80 crosses a normalized slope threshold 84. Each of slope crossing frames 82 is either an increasing crossing frame, or a decreasing crossing frame. An increasing slope crossing frame 82 is where normalized slope 80 is increasing when normalized slope 80 crosses threshold 84. A decreasing crossing frame 82 is where normalized slope 80 is decreasing when normalized slope 80 crosses threshold 84. As discussed above in connection with the step 418 determination of crossing frames 74, a "crossing" of normalized slope 80 with a threshold 84 might not involve locating a frame where normalized slope 80 is exactly equal to threshold 84. Instead, any of the techniques described above for detecting the step 418 crossing frames may be applied to detect the slope crossing frames 82 in step 434. s Threshold 84 may be a configurable parameter of method 400 and may be determined empirically.

Method 400 then enters a loop 450 which is performed once per each rep in rep videos 78 (i.e. for each rep between each start frame 76A and end frame 76B). Step 436 of method 400 comprises determining if the first slope crossing frame of crossing frames 82 in a rep is an increasing crossing frame 82. If the first slope crossing frame 82 is an increasing slope crossing frame 82, then method 400 proceeds to step 440. If the first slope crossing frame 82 is not an increasing slope crossing frame 82, then method 400 proceeds to step 438.

Step 440 of method 400 comprises changing the rep start frame 76A to be the first slope-crossing frame 82 (and discarding frames preceding the new rep start frame 76A) if the slope at the first slope-crossing frame 82 is an increasing slope crossing frame 82. This step 440 procedure effectively temporally crops beginning (rep start frame 76A) of the current rep even further within rep video 78.

Whether arriving from step 436 or from step 440, method 400 proceeds to step 438 which comprises determining if the last slope crossing frame 82 in a rep is a decreasing slope crossing frame 82. If the last slope crossing frame 82 is a decreasing slope crossing frame 82, then method 400 proceeds to step 442. If the last slope crossing frame 82 is not a decreasing slope crossing frame 82, then method 400 is finished for the current rep and loops back to block 436 (not shown) to determine if the next rep can be further temporally cropped. If the last slope crossing frame 82 is not a decreasing slope crossing frame 82 and the current rep is the last rep in rep video 78, then method 400 ends with the start frames 76A and end frames 76B determined for each rep.

Step 442 of method 400 comprises changing the rep end frame 76B to be the last slope-crossing frame 82 (and discarding frames following the new rep end frame 76B) if the slope at the last slope-crossing frame 82 is a decreasing slope crossing frame 82. This step 442 procedure may effectively temporally crop the end (rep end frame 76B) of the current rep even furthering within rep video 78.

Figure 4C:
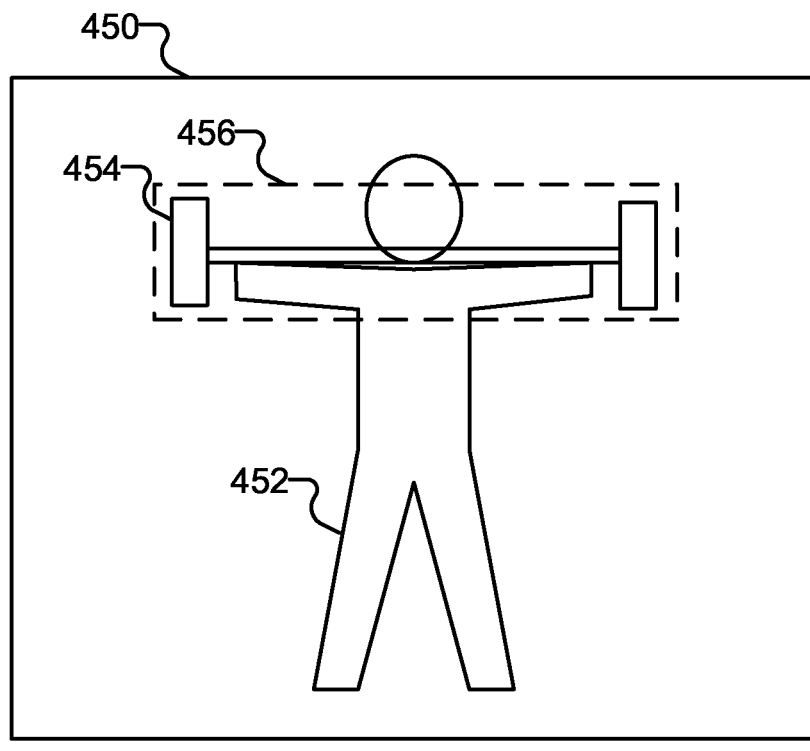
FIGS. 4C and 4D are schematic views of identifying an object region and calculating an object height, according to one embodiment of the present invention.
Figure 4D:
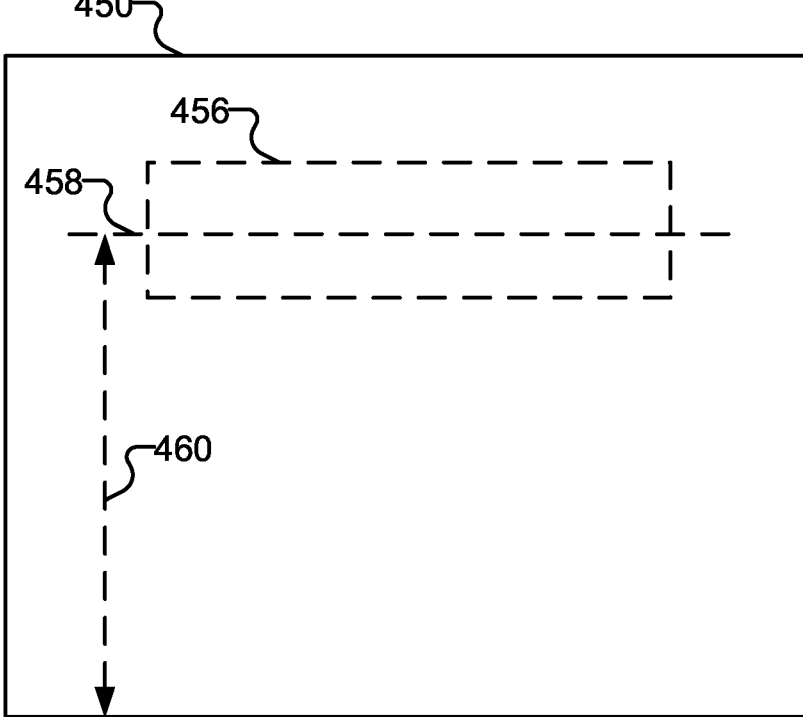

FIGS. 4C and 4D are schematic views of identifying an object region and calculating an object height, according to one embodiment of the present invention.

FIG. 4C depicts an example video frame 450 of individual 452 performing an exercise rep of an exercise type. As depicted in FIG. 4C, the exercise type is one involving barbell 454. A barbell may be designated as the exercise object for the exercise type.

Bounding box 456 containing exercise object 454 may be generated for frame 450. Bounding box 456 may be generated by object detection model (e.g. in block 410) which receives video frame 450 and is trained to identify a barbell 454. The object detection model may identify barbell 454 and generate bounding box 456 from identified barbell 454.

FIG. 4D depicts an average object height 460 of bounding box 456. Average object height 460 may be calculated by averaging a top and a bottom of bounding box 456. Object height 460 may be the distance between a bottom of frame 450 and average object height 460. As discussed elsewhere herein, other aspects of bounding box 456 may be used to determine object height 460.

Figure 5A:
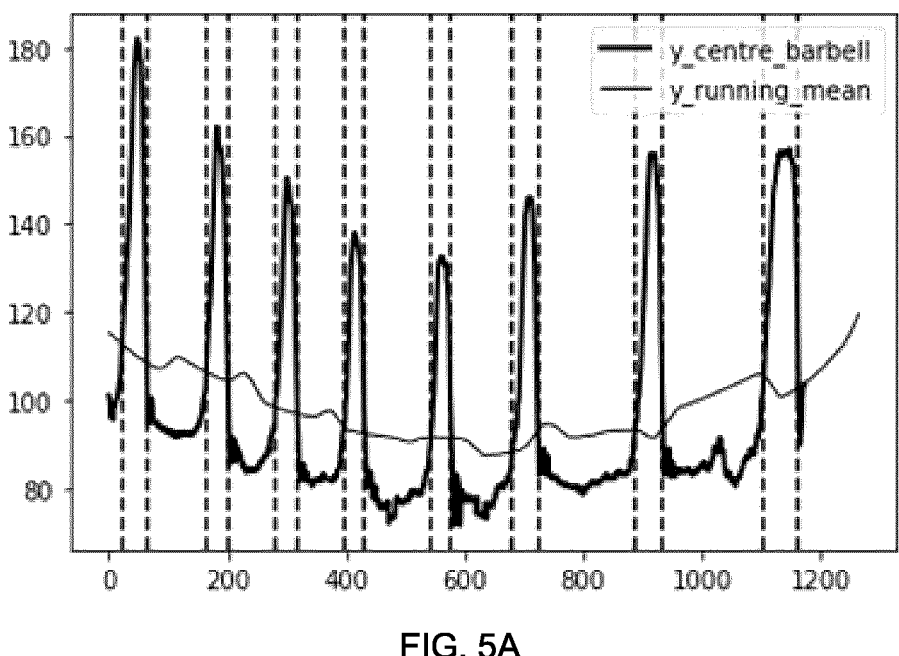
FIGS. 5A to 5N are graphical representations of examples of method 400.
Figure 5B:
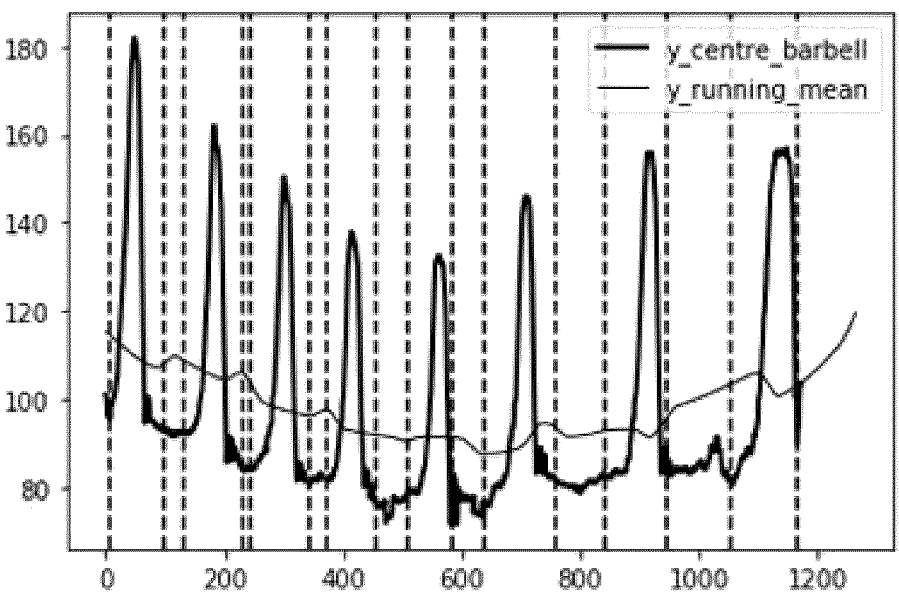
Figure 5C:
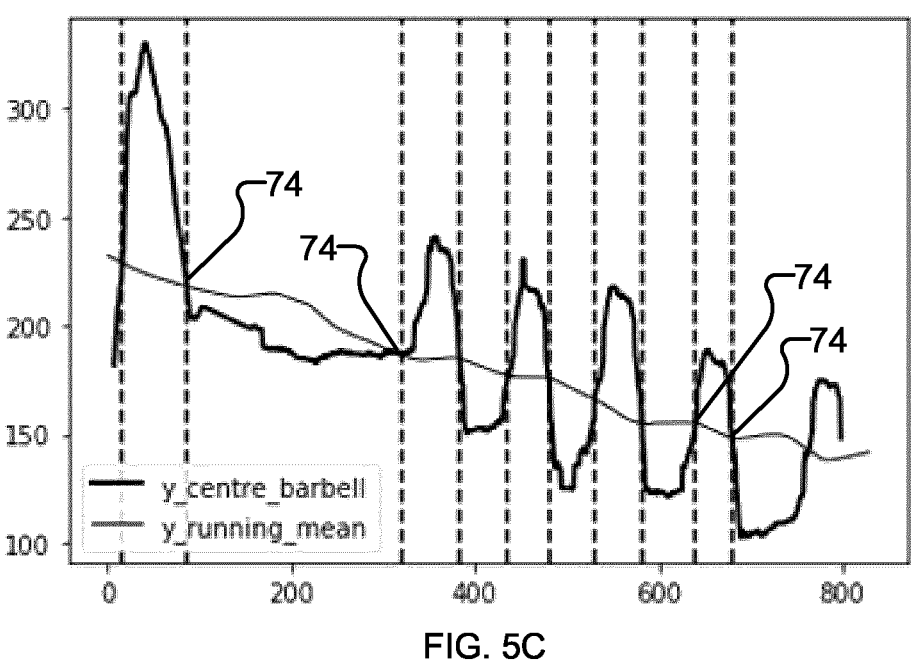
Figure 5D:
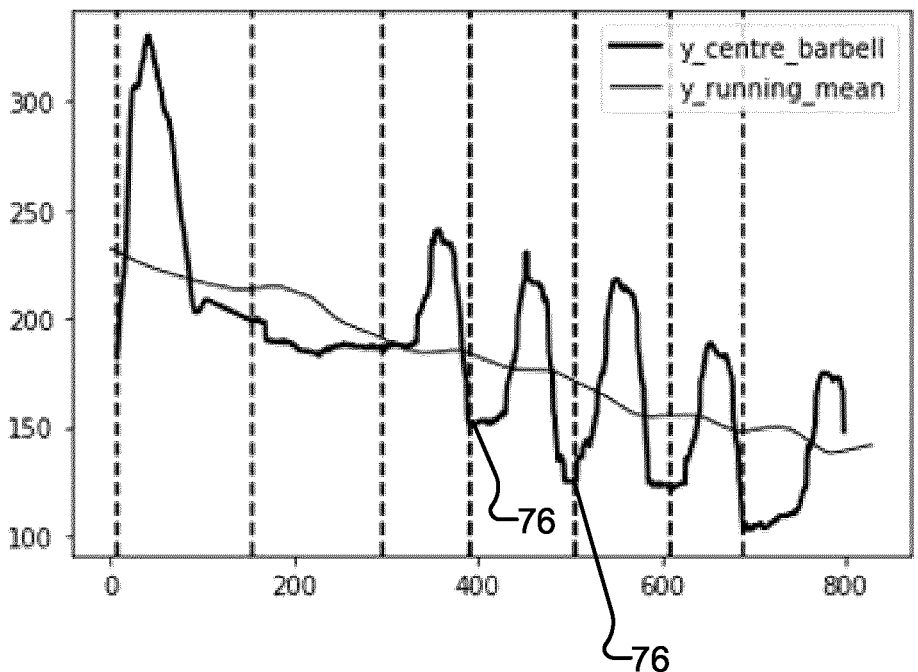
Figures 5E, 5F:
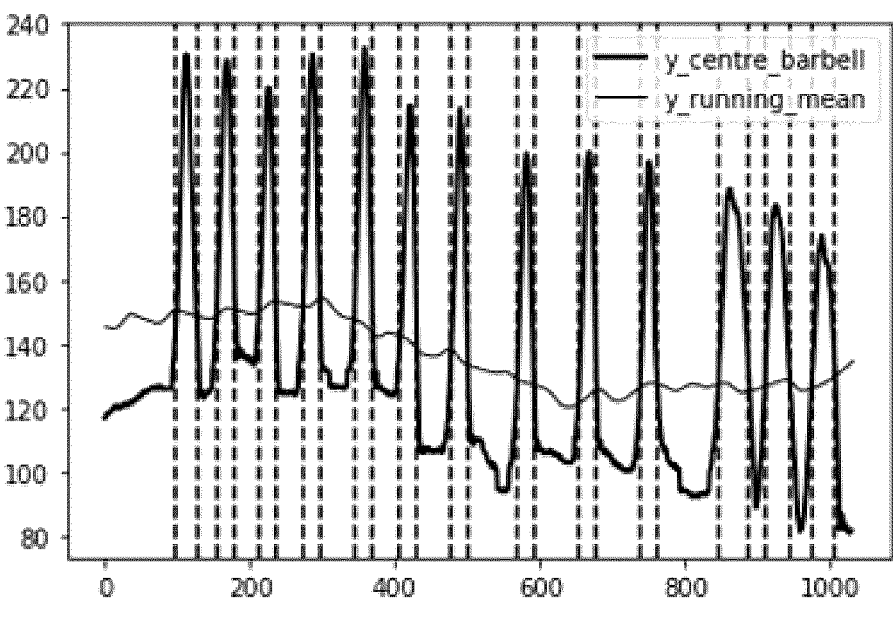
Figure 5G:
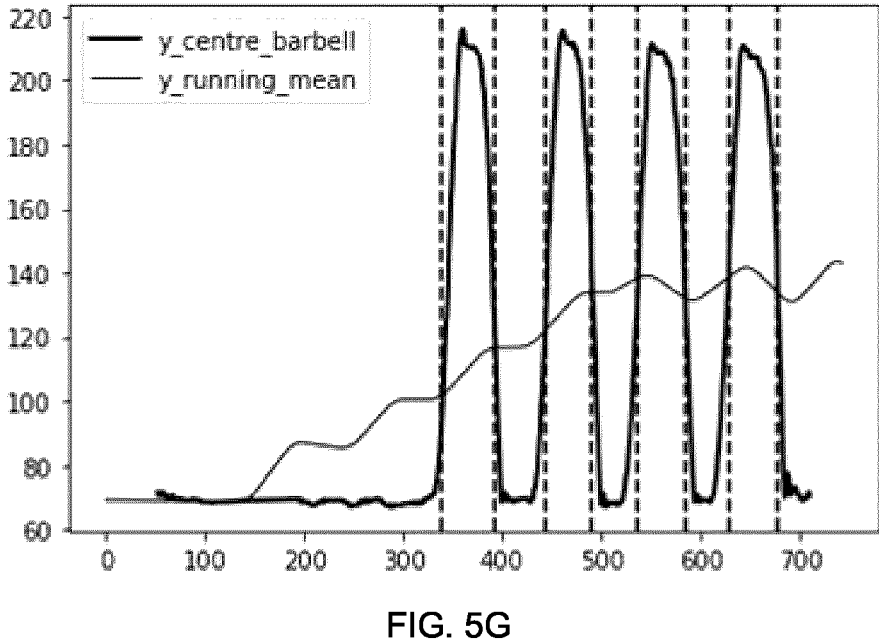
Figure 5H:
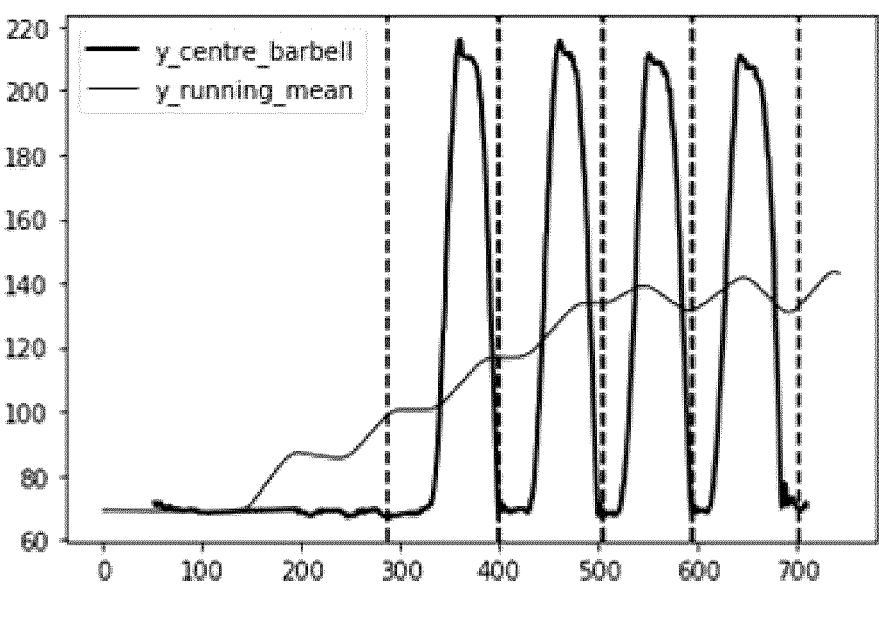
Figures 5I, 5J:
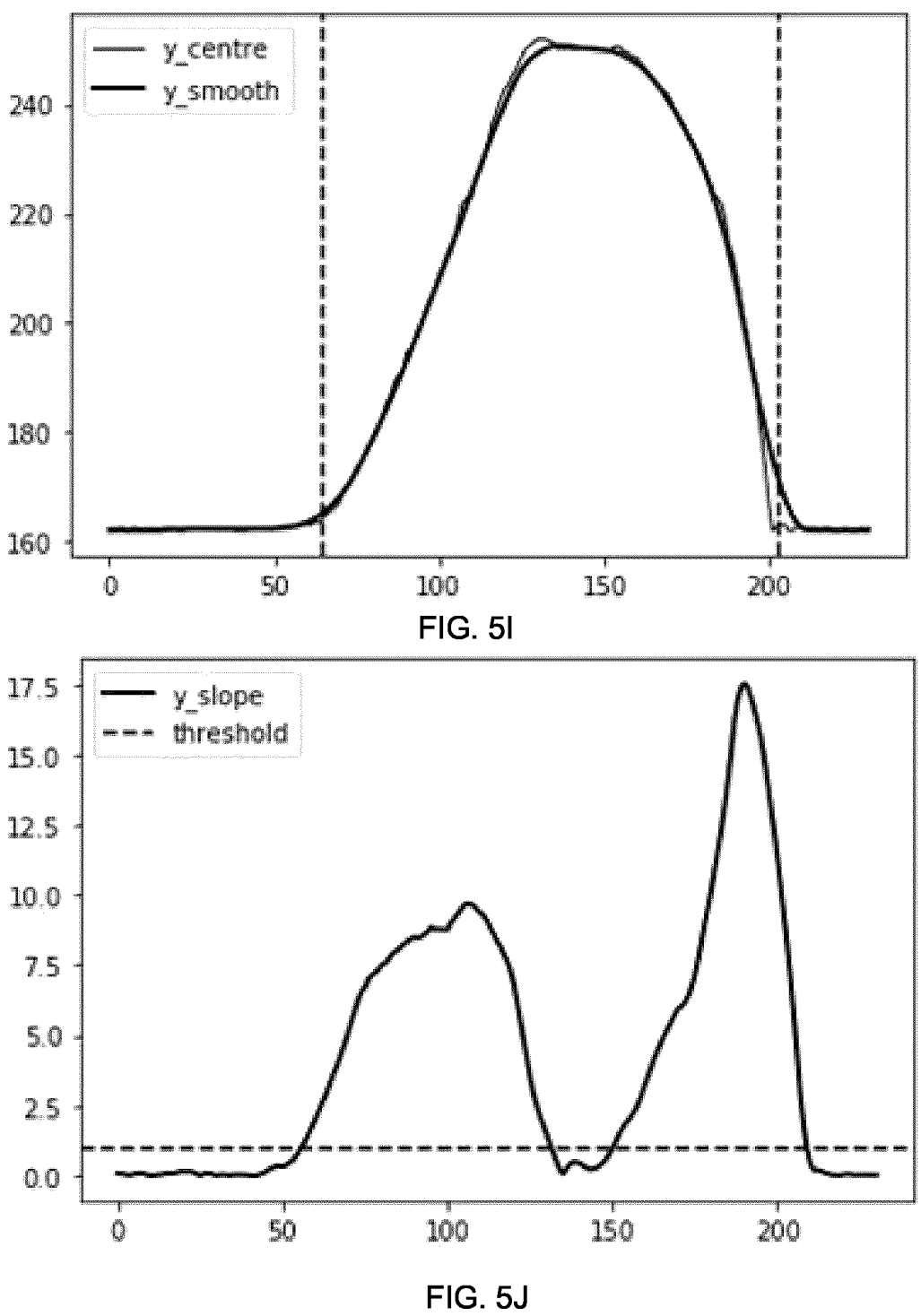
Figures 5K, 5L:
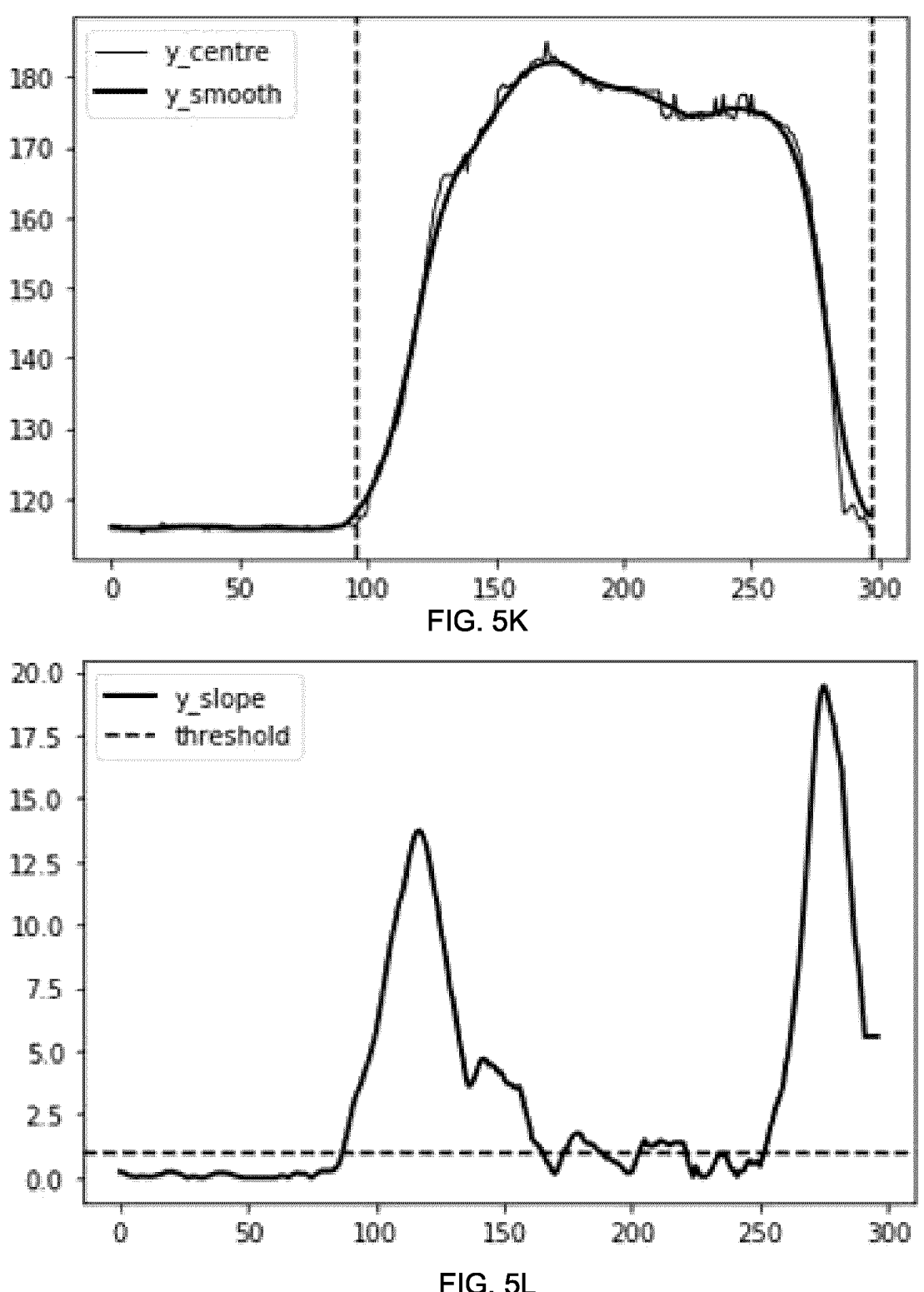
Figures 5M, 5N:
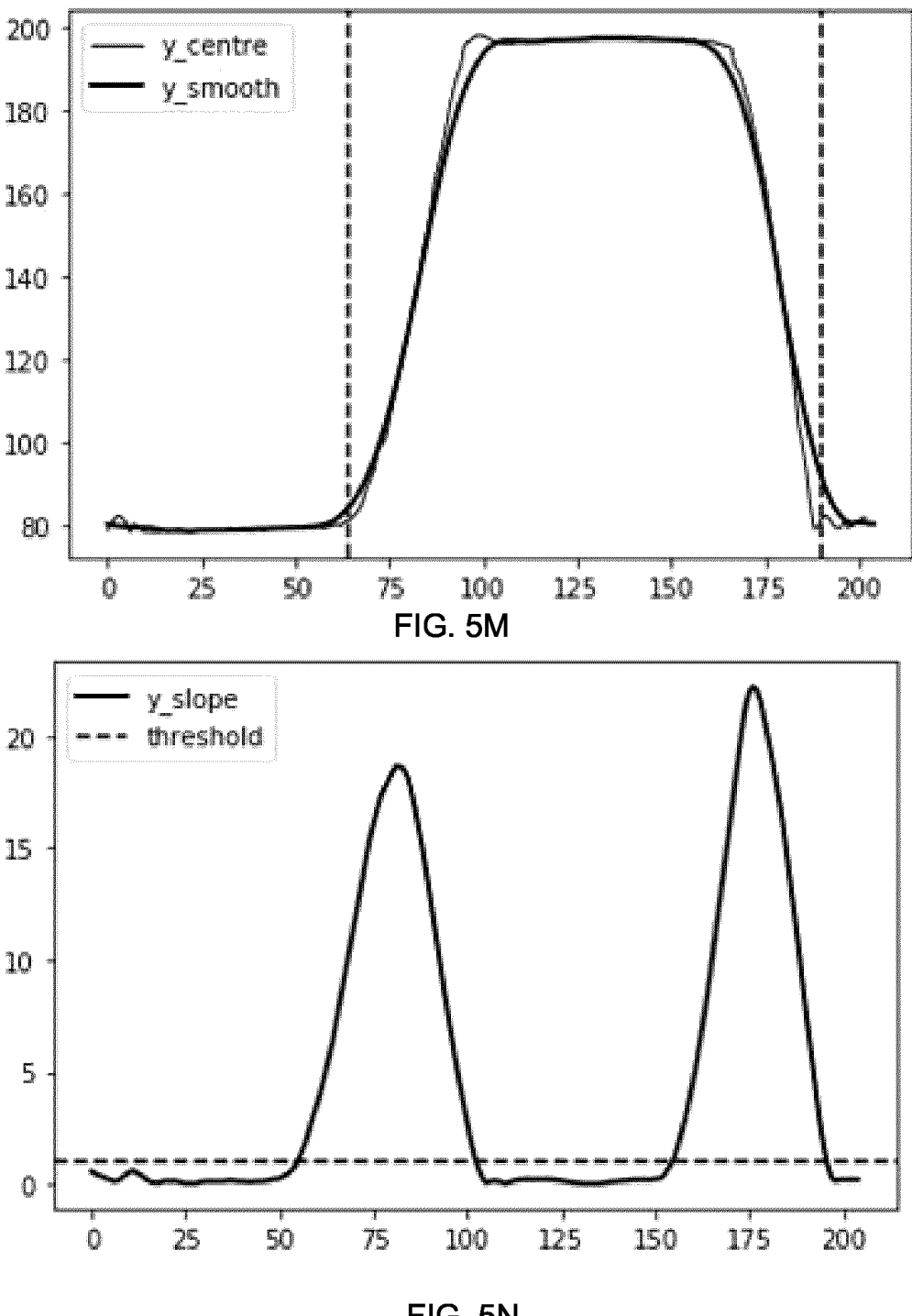

FIGS. 5A to 5N are graphical representations of an example of method 400.

FIGS. 5A to 5H depict example graphs of the height of a center of a barbell and a running average of barbell height versus frame number for multiple videos of reps of various exercise types involving raising and lowering a barbell. FIGS. 5A, 5C, 5E and 5G depict crossing fames 74 (a number of which are enumerated in FIG. 5C) where the barbell height crosses the running average as dashed vertical lines. FIGS. 5B, 5D, 5F and 5I (which correspond respectively to FIGS. 5A, 5C, 5E and 5G) depict minima frames 76 (a number of which are enumerated in FIG. 5D) where the barbell height is a minimum between a crossing frame pair as dashed vertical lines.

FIGS. 5I, 5K and 5M depict example graphs of the smoothed height of the barbell for a rep and FIGS. 5J, 5L and 5N (which corresponding respectively to FIGS. 5I, 5K and 5M) depict the absolute value of the normalized slope of the barbell height and the slope threshold 84 (depicted as a dashed horizontal lines) for these reps. The slope crossing frames 82 are show in FIGS. 5I, 5K and 5M as vertical dashed lines. FIGS. 5I-5N show how the start frame 76A and the end frame 76B can be further temporally cropped to the slope crossing frames 82 (shown in FIGS. 5I, 5K and 5M as vertical dashed lines) using the procedure of method 400.

Embodiments of the invention have been described above in the context of physical exercise involving repetitive movements or reps. Embodiments of the present invention may provide corrective feedback for any physical movement, for example sport movements such as: swinging a golf club, swinging a tennis racking, shooting a basketball or swinging a baseball bat. Embodiments of the invention have been described using exercise equipment (e.g. a barbell). This is not necessary and it will be appreciated that the systems and methods described herein can be used for body weight exercises or the like (e.g. pull ups, push ups, lunges and/or the like). Embodiments of the present invention may also provide corrective feedback for static exercises involving isometric muscle contract (e.g. that do not strictly involve reps), such as stretching, yoga poses, planks and/or the like.

The technology herein can be implemented on various mediums of computer hardware. Specifically, the various components of the implementation can be performed by computing devices of varying complexity with satisfactory processing capacity to execute the implementation. Examples of these devices might include: smartphones, server computers, desktop PCs, laptops and tablet computers. Furthermore, the various actions carried out by the implementation may be distributed across multiple devices. For instance, one device may preprocess the video for a given machine learning algorithm, one more other devices may generate outputs by running one or more machine learning algorithms, other devices may handle the merging and further processing of output from one or more machine learning algorithms, and one or more other devices may communicate outputs to one or more other devices, for example the video input device.

Any implementation that relies on other software components already in existence (e.g. standard mathematical operations), it is assumed that these functions are accessible to a skilled programmer. These functions, as well as scripting functions and other basic functions may be implemented in any number of programming languages. One or more feature of the present disclosure may be implemented with C, C++, Java, Python, Perl, R, or any other equivalent programming language. It should also be noted that the present disclosure is not limited by or dependent on the programming language or languages used to implement any basic functions.

The technology herein can be implemented to run on any of the widely used computer operating systems currently in use. A partial list of these operating systems and some of their associated version names include: Windows Phone, Windows Mobile, Windows 97, Windows 2000, Windows 10, Apple iOS 12, Apple iOS 11, Apple iOS 10, Apple Macintosh OS X Mountain Lion, Apple Macintosh OS X Leopard, Apple Macintosh OS X Tiger, UNIX Berkley Standard operating system, the Linux operating system, and the Android operating systems.

It should be noted that the executable instructions that allow a computer of suitable configuration to carry out the required methods for evaluating an individual's exercise form can be stored in any computer-readable storage medium. The storage medium might include: an external hard drive, USB thumb drive, CD-Rom, or the like. Furthermore, the executable instructions can be stored in any portable computer storage device in order to be delivered to a user. Additionally, the executable instructions can be downloaded remotely by an end-user onto their own computer given an internet connection (e.g. either ethernet or WiFi). However, this option does not assume that the executable instructions are represented as a signal. The executable instructions may also be run on a cloud-based computer system or virtual machine.

An exemplary embodiment of the technology herein utilizes a smartphone's camera for video recording in conjunction with the smartphone's memory storage and communication links (i.e. WiFi, Bluetooth, or other mode of data transportation). The raw data produced by the smartphone includes video of a user performing exercise.

The example movement that will be referenced throughout this rationale to describe the array of measurable parameters is a back squat. This exercise movement has the user standing with feet shoulder-distance apart with a barbell resting parallel to the ground on the user's upper back. As the user performs the exercise, the user's knees and hips bend as the user lowers their rear as if sitting in a chair. The user stops descent once the tops of the user's thighs are parallel to the ground or lower. The user then reverses the motion and direction of forces exerted in order to return to a standing position.

Throughout the evaluation of an exercise movement, the data extracted from the video input provides information about location of individual, body part locations, angles of joints, etc. This information can be derived from the video input using an object detection model to identify a user, the location of relevant body parts, and a barbell. Then the barbell's vertical position can be used to separate individual repetitions. Then for each error to be detected, videos are spatially cropped such that they contain the relevant regions (body parts) to identify respective errors. The cropped videos are then formatted to match the same format used by the original training of the error detection model to evaluate the body movements. These error detection models identify the presence of respective errors. For example, if a user's chest is identified as not being upright enough, the user may be placing unnecessary stress on their lumbar spine.

Once any issues with the individual's exercise form have been identified, then feedback can be provided back to the individual regarding whether the individual's form is correct or not. Furthermore, the feedback will convey to the user what they can focus on while completing the exercise movement in the future in order to improve back squat form.

Interpretation of Terms

Unless the context clearly requires otherwise, throughout the description and the "comprise", "comprising", and the like are to be construed in an inclusive sense, as opposed to an exclusive or exhaustive sense; that is to say, in the sense of "including, but not limited to";

"connected", "coupled", or any variant thereof, means any connection or coupling, either direct or indirect, between two or more elements; the coupling or connection between the elements can be physical, logical, or a combination thereof;

"herein", "above", "below", and words of similar import, when used to describe this specification, shall refer to this specification as a whole, and not to any particular portions of this specification;

"or", in reference to a list of two or more items, covers all of the following interpretations of the word: any of the items in the list, all of the items in the list, and any combination of the items in the list;

the singular forms "a", "an", and "the" also include the meaning of any appropriate plural forms.

Words that indicate directions such as "vertical", "transverse", "horizontal", "upward", "downward", "forward", "backward", "inward", "outward", "vertical", "transverse", "left", "right", "front", "back", "top", "bottom", "below", "above", "under", and the like, used in this description and any accompanying claims (where present), depend on the specific orientation of the apparatus described and illustrated. The subject matter described herein may assume various alternative orientations. Accordingly, these directional terms are not strictly defined and should not be interpreted narrowly.

Embodiments of the invention may be implemented using specifically designed hardware, configurable hardware, programmable data processors configured by the provision of software (which may optionally comprise "firmware") capable of executing on the data processors, special purpose computers or data processors that are specifically programmed, configured, or constructed to perform one or more steps in a method as explained in detail herein and/or combinations of two or more of these. Examples of specifically designed hardware are: logic circuits, application-specific integrated circuits ("ASICs"), large scale integrated circuits ("LSIs"), very large scale integrated circuits ("VLSIs"), and the like. Examples of configurable hardware are: one or more programmable logic devices such as programmable array logic ("PALs"), programmable logic arrays ("PLAs"), and field programmable gate arrays ("FPGAs")). Examples of programmable data processors are: microprocessors, digital signal processors ("DSPs"), embedded processors, graphics processors, math co-processors, general purpose computers, server computers, cloud computers, mainframe computers, computer workstations, and the like. For example, one or more data processors in a control circuit for a device may implement methods as described herein by executing software instructions in a program memory accessible to the processors.

Processing may be centralized or distributed. Where processing is distributed, information including software and/or data may be kept centrally or distributed. Such information may be exchanged between different functional units by way of a communications network, such as a Local Area Network (LAN), Wide Area Network (WAN), or the Internet, wired or wireless data links, electromagnetic signals, or other data communication channel.

For example, while processes or steps are presented in a given order, alternative examples may perform routines having steps, or employ systems having steps, in a different order, and some processes or steps may be deleted, moved, added, subdivided, combined, and/or modified to provide alternative or subcombinations. Each of these processes or steps may be implemented in a variety of different ways. Also, while processes or steps are at times shown as being performed in series, these processes or steps may instead be performed in parallel, or may be performed at different times.

In addition, while elements are at times shown as being performed sequentially, they may instead be performed simultaneously or in different sequences. It is therefore intended that the following claims are interpreted to include all such variations as are within their intended scope.

Software and other modules may reside on servers, workstations, personal computers, tablet computers, image data encoders, image data decoders, PDAs, color-grading tools, video projectors, audio-visual receivers, displays (such as televisions), digital cinema projectors, media players, and other devices suitable for the purposes described herein. Those skilled in the relevant art will appreciate that aspects of the system can be practised with other communications, data processing, or computer system configurations, including: Internet appliances, hand-held devices (including personal digital assistants (PDAs)), wearable computers, all manner of cellular or mobile phones, multi-processor systems, microprocessor-based or programmable consumer electronics (e.g., video projectors, audio-visual receivers, displays, such as televisions, and the like), set-top boxes, color-grading tools, network PCs, mini-computers, mainframe computers, and the like.

The invention may also be provided in the form of a program product. The program product may comprise any non-transitory medium which carries a set of computer-readable instructions which, when executed by a data processor, cause the data processor to execute a method of the invention. Program products according to the invention may be in any of a wide variety of forms. The program product may comprise, for example, non-transitory media such as magnetic data storage media including floppy diskettes, hard disk drives, optical data storage media including CD ROMs, DVDs, electronic data storage media including ROMs, flash RAM, EPROMs, hardwired or preprogrammed chips (e.g., EEPROM semiconductor chips), nanotechnology memory, or the like. The computer-readable signals on the program product may optionally be compressed or encrypted.

In some embodiments, the invention may be implemented in software. For greater clarity, "software" includes any instructions executed on a processor, and may include (but is not limited to) firmware, resident software, microcode, and the like. Both processing hardware and software may be centralized or distributed (or a combination thereof), in whole or in part, as known to those skilled in the art. For example, software and other modules may be accessible via local memory, via a network, via a browser or other application in a distributed computing context, or via other means suitable for the purposes described above.

Where a component (e.g. a software module, processor, assembly, device, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

Specific examples of systems, methods and apparatus have been described herein for purposes of illustration. These are only examples. The technology provided herein can be applied to systems other than the example systems described above. Many alterations, modifications, additions, omissions, and permutations are possible within the practice of this invention. This invention includes variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments.

Various features are described herein as being present in "some embodiments". Such features are not mandatory and may not be present in all embodiments. Embodiments of the invention may include zero, any one or any combination of two or more of such features. This is limited only to the extent that certain ones of such features are incompatible with other ones of such features in the sense that it would be impossible for a person of ordinary skill in the art to construct a practical embodiment that combines such incompatible features. Consequently, the description that "some embodiments" possess feature A and "some embodiments" possess feature B should be interpreted as an express indication that the inventors also contemplate embodiments which combine features A and B (unless the description states otherwise or features A and B are fundamentally incompatible).

It is therefore intended that the following appended claims and claims hereafter introduced are interpreted to include all such modifications, permutations, additions, omissions, and sub-combinations as may reasonably be inferred. The scope of the claims should not be limited by the preferred embodiments set forth in the examples, but should be given the broadest interpretation consistent with the description as a whole.

The invention claimed is:

1. A method of generating user feedback from video of a user performing one or more reps of an exercise type, the method comprising:

receiving an exercise type;

selecting a rep detection model from a plurality of rep detection models, wherein the selected rep detection model corresponds to the exercise type;

selecting an error indication model from a plurality of error indication models, wherein the selected error indication model corresponds to the exercise type and comprises a machine learning algorithm trained on videos of individuals performing the exercise type;

receiving a video of a user performing one or more reps of the exercise type;

cropping the video to a specific aspect ratio;

identifying a plurality of frames in the video corresponding to a rep of the exercise type with the selected rep detection model;

generating a form error indication for the rep with the selected error indication model; and generating feedback based on the form error indication;

wherein generating the form error indication for the detected rep with the selected error indication model comprises:

generating an error indication for each of the plurality of frames corresponding to the rep; and generating the form error indication based at least in part on the error indication for at least one of the plurality of frames corresponding to the rep.

2. The method according to claim 1, wherein receiving the exercise type comprises receiving a user selection of one of a plurality of exercise types.

3. The method according to claim 1, wherein receiving the exercise type comprises generating an exercise type for the video with an exercise classification model.

4. The method according to claim 1, wherein receiving the video of the user performing one or more reps of the exercise type comprises capturing video of the user performing the reps with a video capture device.

5. The method according to claim 1, wherein the specific aspect ratio is one pixel by one pixel.

6. The method according to claim 1, wherein the error indication for each frame of the rep comprises an error probability, and generating the form error indication based at least in part on the error indication for at least one frame of the rep comprises generating a form error indication indicating the presence of an error if the error probability for at least one frame of the rep exceeds a probability threshold.

7. The method according to claim 1, wherein the error indication for each frame of the rep comprises an error probability, and generating the form error indication based at least in part on the error indication for at least one frame of the rep comprises generating a form error indication indicating the presence of an error if the error probability for a threshold number of frames of the rep exceed a probability threshold.

8. The method according to claim 1, wherein the error indication for each frame of the rep comprises an error probability, and generating the form error indication based at least in part on the error indication for at least one frame of the rep comprises generating a form error indication indicating the presence of an error if the error probability for a threshold number of consecutive frames of the rep exceed a probability threshold.

9. The method according to claim 1, wherein the error indication for each frame of the rep comprises an error probability, and generating the form error indication based at least in part on the error indication for at least one frame of the rep comprises:

calculating a sum of the error probabilities of the frames of the rep; and generating a form error indication indicating the presence of an error if the sum of the error probabilities exceeds a probability threshold.

10. The method according to claim 1, wherein generating feedback based on the form error indication comprises selecting a media file corresponding to an error type of the error indication model if the form error indication indicates the presence of an error in the rep.

11. The method according to claim 10, wherein the media file comprises video of an individual demonstrating an error of the error type.

12. The method according to claim 10, wherein the media file comprises corrective audio instructions.

13. The method according to claim 10, wherein the media file comprises corrective video instructions.

14. A non-transitory medium having stored thereon computer-readable instructions, which when executed by a data processor, cause the data processor to execute the method according to claim 5.

15. A method according to claim 5, wherein the exercise type is one of: squats, deadlifts, pull-ups, push-ups, bench presses, planks, bicep curls, and a yoga pose.

16. The method according to claim 1, wherein the selected error indication model is configured to identify a body part of the user, and generating the form error indication for the detected rep with the selected error indication model further comprises:

identifying a position of the body part of the user in one of the plurality of frames; and generating the form error indication based on the position of the body part of the user.

17. The method according to claim 1, wherein the selected error indication model is configured to identify an exercise equipment, and generating the form error indication for the detected rep with the selected error indication model further comprises:

identifying the exercise equipment in one of the plurality of frames; and generating the form error indication based on the identified exercise equipment.

18. A method of generating user feedback from video of a user performing one or more reps of an exercise type, the method comprising:

receiving an exercise type;

selecting a rep detection model from a plurality of rep detection models, wherein the selected rep detection model corresponds to the exercise type;

selecting an error indication model from a plurality of error indication models, wherein the selected error indication model corresponds to the exercise type and comprises a machine learning algorithm trained on videos of individuals performing the exercise type;

receiving a video of a user performing one or more reps of the exercise type;

adding pixels to the video to format the video to a specific aspect ratio;

identifying a plurality of frames in the video correspond-
ing to a rep of the exercise type with the selected rep
detection model;
generating a form error indication for the rep with the
selected error indication model; and
generating feedback based on the form error indication;
wherein generating the form error indication for the
detected rep with the selected error indication model
comprises:
generating an error indication for each of the plurality of
frames corresponding to the rep; and
generating the form error indication based at least in part
on the error indication for at least one of the plurality
of frames corresponding to the rep.

19. A system for providing feedback to a user performing
one or more reps of an exercise type, the system comprising:
a video capture device;
a processor;
a memory module;
an input module; and
an output module;
wherein the processor is configured to:
receive an exercise type;
capture video of the user performing one or more reps of
the exercise type with the video capture device;
retrieve a rep detection model corresponding to the exer-
cise type from the memory module;
crop the video to a specific aspect ratio;

execute the rep detection model to identify a plurality of
frames in the video corresponding to a rep of the
exercise type;
retrieve an error indication model corresponding to the
exercise type from the memory module, wherein the
error indication model comprises a machine learning
algorithm trained on videos of individuals performing
the exercise type;
execute the error indication model to generate a form
error indication for the identified rep; and
output feedback with the output module based on the form
error indication;
wherein the processor is configured to:
execute the error indication model to generate a form
error indication for each of the plurality of frames
corresponding to the rep; and
generate the form error indication based at least in part
on the error indication for at least one of the plurality
of frames corresponding to the rep.

20. The system according to claim 19, wherein the pro-
cessor is configured to receive the exercise type from the
input module.

21. The system according to claim 19, wherein the pro-
cessor is configured to:
retrieve an exercise classification model from the memory
module; and
execute the exercise classification model to generate the
exercise type from the video.

* * * * *